(12) United States Patent
Cox et al.

(10) Patent No.: US 11,511,097 B2
(45) Date of Patent: Nov. 29, 2022

(54) PORT TUNNELING SYSTEMS AND METHODS THEREOF

(71) Applicant: C. R. Bard, Inc., Franklin Lakes, NJ (US)

(72) Inventors: Jeremy B. Cox, Salt Lake City, UT (US); James D. Meler, II, Phoenix, AZ (US); Michael Randall, Tempe, AZ (US); Chad Van Liere, Tempe, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 347 days.

(21) Appl. No.: 16/646,119

(22) PCT Filed: Sep. 15, 2017

(86) PCT No.: PCT/US2017/051934
§ 371 (c)(1),
(2) Date: Mar. 10, 2020

(87) PCT Pub. No.: WO2019/055037
PCT Pub. Date: Mar. 21, 2019

(65) Prior Publication Data
US 2020/0269031 A1    Aug. 27, 2020

(51) Int. Cl.
*A61M 39/04* (2006.01)
*A61M 39/22* (2006.01)
*A61M 39/02* (2006.01)

(52) U.S. Cl.
CPC ............ *A61M 39/04* (2013.01); *A61M 39/22* (2013.01); *A61M 2039/0205* (2013.01);
(Continued)

(58) Field of Classification Search
CPC .. A61M 2039/0282; A61M 2039/0294; A61M 39/02; A61M 2039/0291;
(Continued)

(56) References Cited

U.S. PATENT DOCUMENTS

| 5,620,119 A | 4/1997 | Keller |
| 5,624,413 A | 4/1997 | Markel et al. |

(Continued)

FOREIGN PATENT DOCUMENTS

DE    102014015316 A1    4/2016

OTHER PUBLICATIONS

PCT/US2017/051934 filed Sep. 15, 2017 International Preliminary Report on Patentability dated Mar. 26, 2020.
(Continued)

*Primary Examiner* — Theodore J Stigell
(74) *Attorney, Agent, or Firm* — Rutan & Tucker LLP

(57) ABSTRACT

Provided herein is a system including, in some embodiments, a streamlined port and a port tunneler. The port includes a septum and a stabilizing element. The septum is disposed over a cavity in a body of the port, and the septum is configured to accept a needle therethrough. The stabilizing element is configured to stabilize the port in vivo and maintain needle access to the septum. The port tunneler includes an adapter and a release mechanism. The adapter is in a distal end portion of the port tunneler, and the adapter is configured to securely hold the port while subcutaneously tunneling the port from an incision site to an implantation site for the port. The release mechanism is configured to release the port from the adapter at the implantation site for the port.

9 Claims, 18 Drawing Sheets

Figure 1:
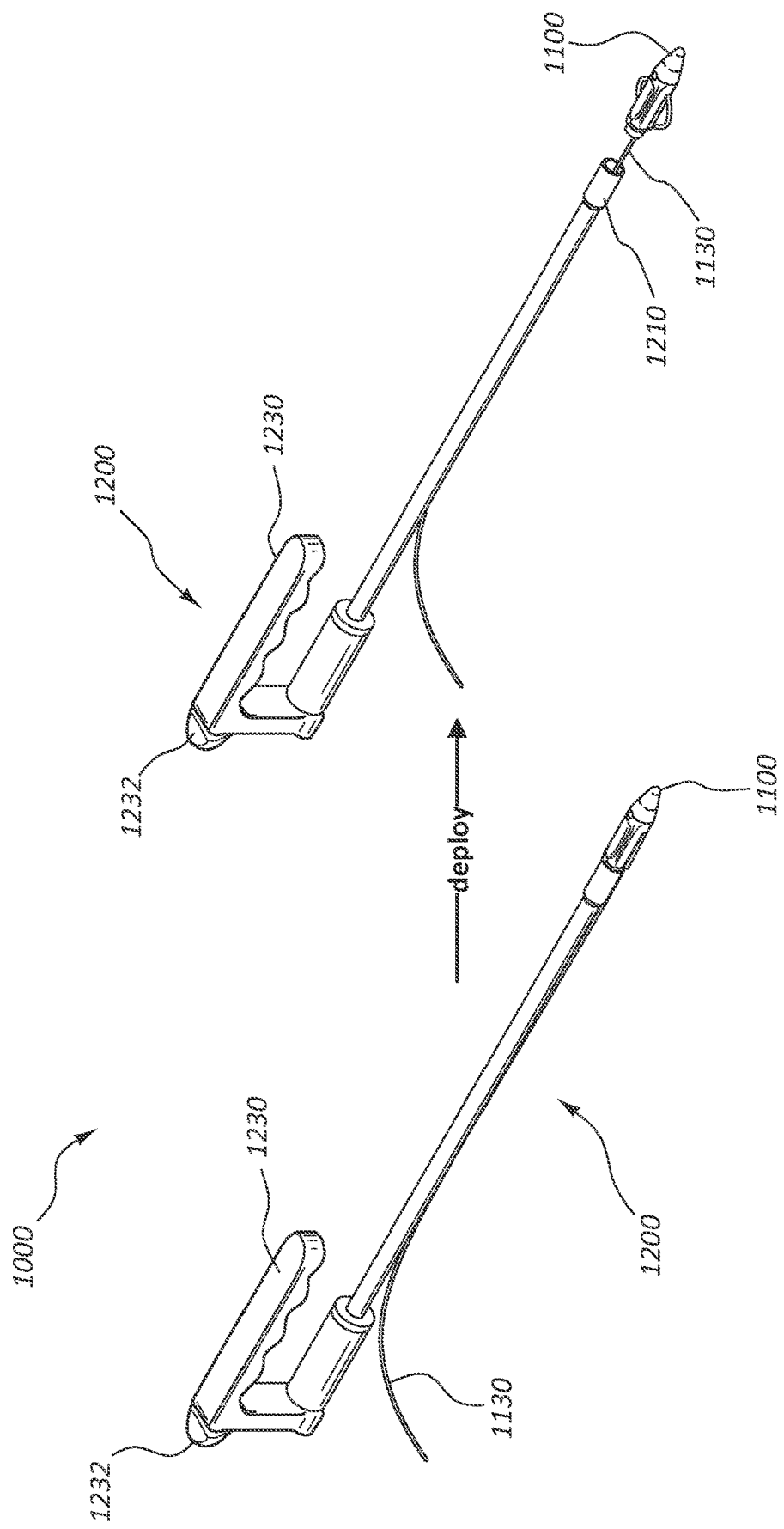

(52) U.S. Cl.
CPC .............. *A61M 2039/0223* (2013.01); *A61M 2039/0291* (2013.01); *A61M 2039/0297* (2013.01)

(58) Field of Classification Search
CPC .. A61M 39/04; A61M 25/0194; A61M 39/22; A61M 2039/0273; A61M 2039/0205; A61M 2039/0297; A61M 2039/0223; A61B 17/3468; A61B 2017/320056
See application file for complete search history.

(56) References Cited

U.S. PATENT DOCUMENTS

| | | | |
|---|---|---|---|
| 5,718,692 A | 2/1998 | Schon et al. | |
| 5,848,989 A | 12/1998 | Villani | |
| 8,876,788 B2 | 11/2014 | Glenn | |
| 9,044,573 B2 | 6/2015 | Ravenscroft et al. | |
| 11,197,687 B2 * | 12/2021 | Ebersole | A61N 1/372 |
| 2003/0088212 A1 | 5/2003 | Tal | |
| 2004/0193119 A1 * | 9/2004 | Canaud | A61M 1/3661 |
| | | | 604/247 |
| 2005/0261664 A1 | 11/2005 | Rome et al. | |
| 2009/0264901 A1 * | 10/2009 | Franklin | A61M 39/0208 |
| | | | 606/139 |
| 2011/0034886 A1 | 2/2011 | Elbe et al. | |
| 2012/0083794 A1 * | 4/2012 | Martin | A61M 25/0194 |
| | | | 606/108 |
| 2013/0012890 A1 * | 1/2013 | Glenn | A61M 39/0208 |
| | | | 604/288.02 |
| 2017/0182304 A1 | 6/2017 | Bagwell et al. | |

OTHER PUBLICATIONS

PCT/US2017/051934 filed Sep. 15, 2017 International Search Report dated Dec. 1, 2017.
PCT/US2017/051934 filed Sep. 15, 2017 Written Opinion dated Dec. 1, 2017.
EP17924863.8 filed Mar. 24, 2020 Extended European Search Report dated Jun. 9, 2020.

* cited by examiner

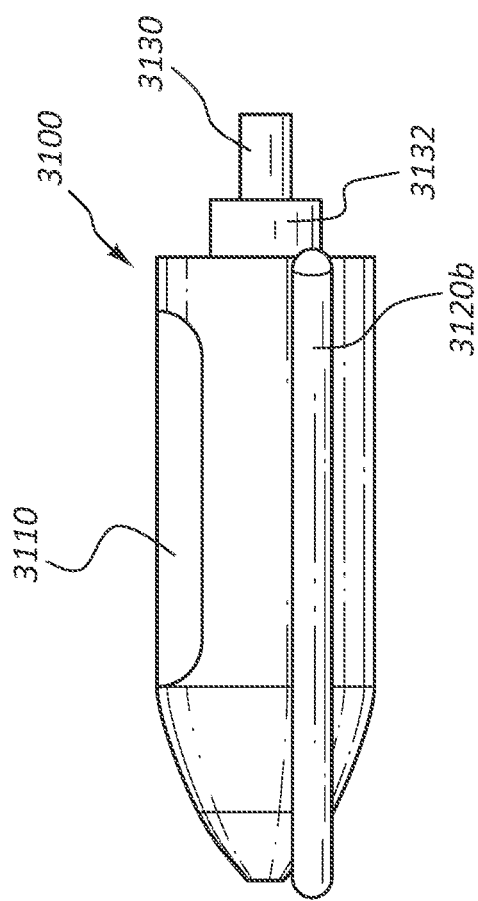
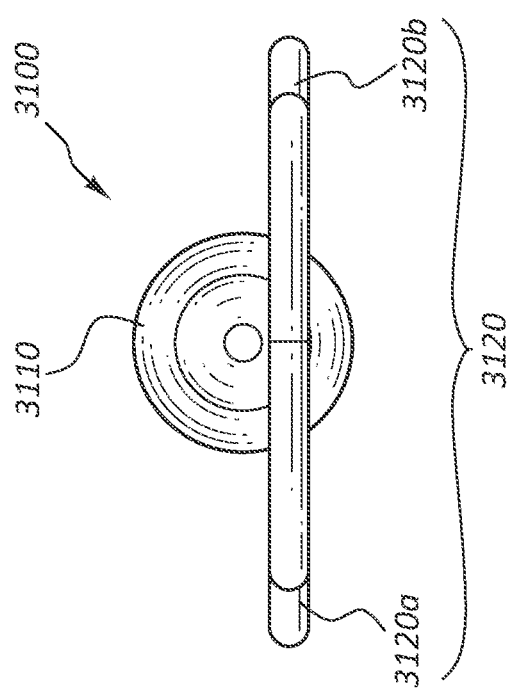
FIG. 3B
FIG. 3A

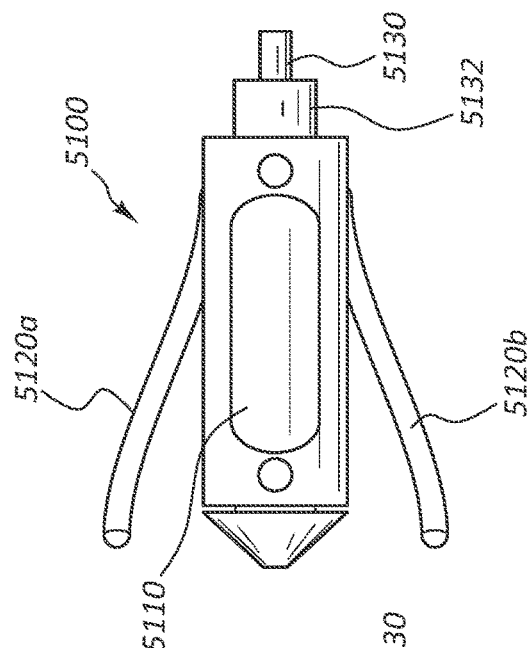
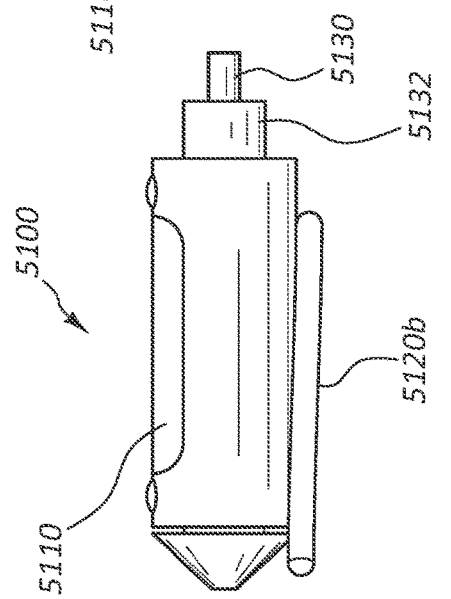
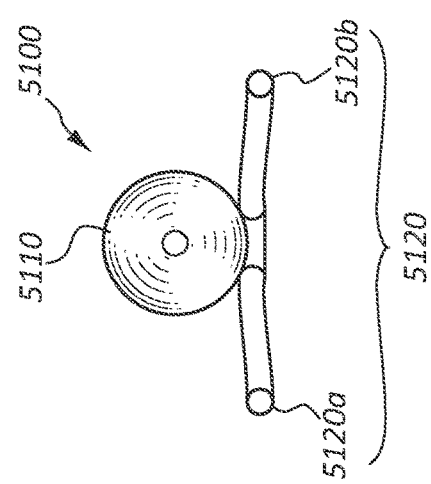
FIG. 5C
FIG. 5B
FIG. 5A

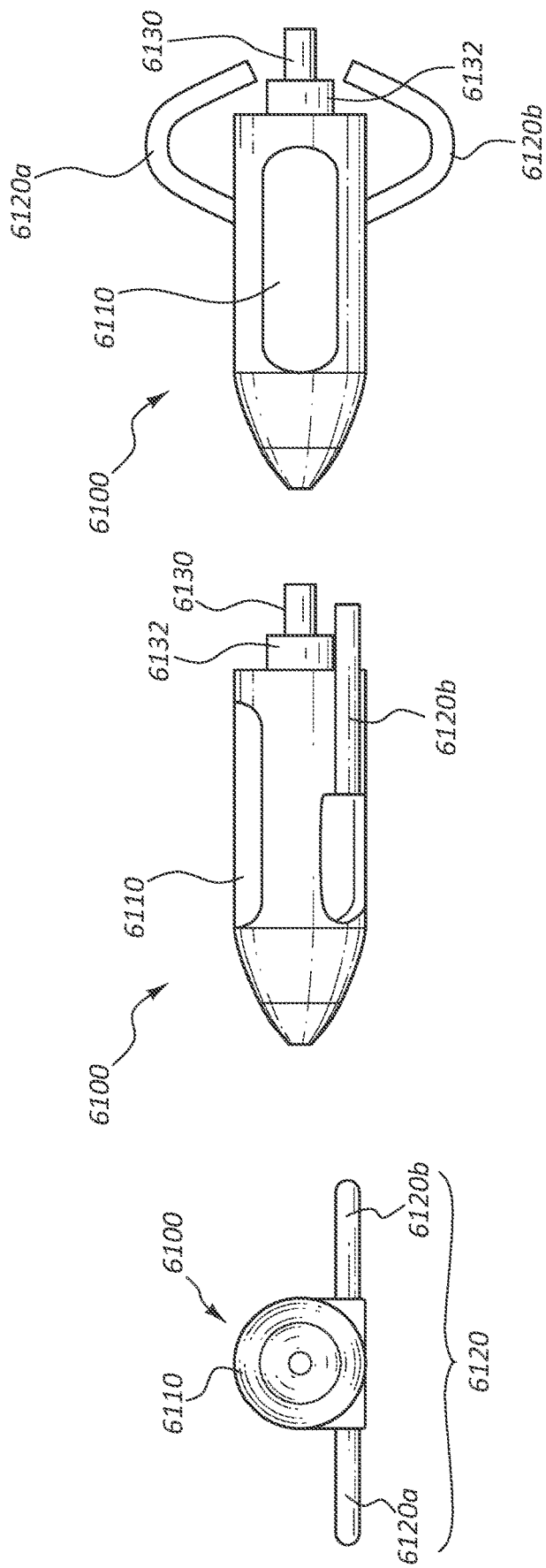

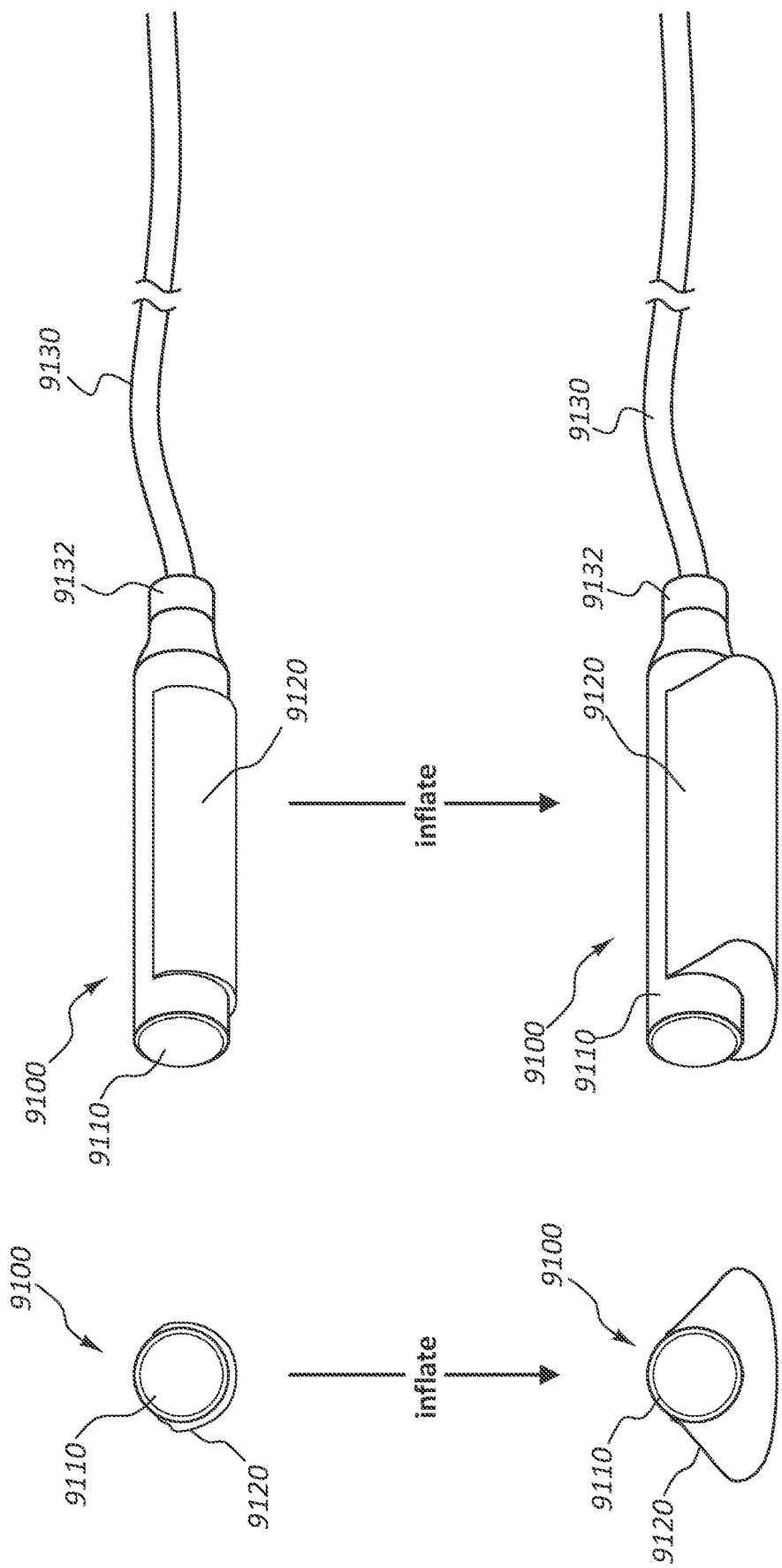

PORT TUNNELING SYSTEMS AND METHODS THEREOF

This application is a U.S. national stage from International Application No. PCT/US2017/051934, filed Sep. 15, 2017, which is incorporated by reference in its entirety into this application.

BACKGROUND

Standard procedure for placing a vascular access device such as a port requires two incisions: a first incision near the clavicle, used to introduce a catheter to the superior vena cava for vascular access, and a second incision lower on the chest, where the port is ultimately implanted in a port pocket and connected to the catheter. Creation and closure of the port pocket accounts for a large percentage (about 42%) of the procedure and increases tissue trauma and risk of infection at the site of the second incision. Furthermore, the requirement for the second incision increases potential for scarring. Provided herein are port tunneling systems and methods that address the foregoing.

SUMMARY

Provided herein is a system including, in some embodiments, a streamlined port and a port tunneler. The port includes a septum and a stabilizing element. The septum is disposed over a cavity in a body of the port, and the septum is configured to accept a needle therethrough. The stabilizing element is configured to stabilize the port in vivo and maintain needle access to the septum. The port tunneler includes an adapter and a release mechanism. The adapter is in a distal end portion of the port tunneler. The adapter is configured to securely hold the port while subcutaneously tunneling the port from an incision site to an implantation site for the port. The release mechanism is configured to release the port from the adapter at the implantation site for the port.

In such embodiments, the stabilizing element is an inflatable section of the port. The inflatable section includes an uninflated state imparting a profile to the port configured for subcutaneously tunneling the port from an incision site to an implantation site for the port. The inflatable section further includes an inflated state configured to stabilize the port from rolling about a central axis of the port in vivo, thereby maintaining needle access to the septum.

In such embodiments, the inflatable section imparts a triangular prismatic-type shape to at least a portion of the port when in the inflated state. A transverse cross section of such a triangular prismatic-type shape is a triangle.

In such embodiments, the inflatable section is configured to inflate with one or more fluids; one or more polymers; or a combination thereof. The one or more fluids are selected from neat fluids and mixtures including solutions.

In such embodiments, the inflatable section is configured to inflate by introducing a solution including at least one polymer precursor that forms a polymer with at least one other polymer precursor after polymerization and cross linking within the inflatable section.

In such embodiments, a swellable polymer is disposed in the inflatable section. The inflatable section is configured to inflate by a combination of introducing water or saline to expand the inflatable section and swelling the swellable polymer with the water or saline to further expand the inflatable section.

In such embodiments, the port tunneler further includes an inflation lumen fluidly connected to the inflatable section for inflating the inflatable section with the one or more fluids.

In such embodiments, the port tunneler further includes a hub at a proximal end of the port tunneler. The hub is configured to fluidly connect with a syringe for delivering the one or more fluids trough the inflation lumen to the inflatable section.

In such embodiments, the port further includes a one-way valve configured to close off the inflation section upon releasing the port from the port tunneler with the release mechanism.

In such embodiments, the stabilizing element is at least a pair of legs. The pair of legs is configured to stabilize the port from rolling about a central axis of the port in vivo, thereby maintaining needle access to the septum.

In such embodiments, the pair of legs is configured to assume a deployed state upon releasing the port from the port tunneler with the release mechanism. The adapter is configured to hold a proximal end portion of the port including the pair of legs in a collapsed state of the pair of legs before releasing the port from the port tunneler with the release mechanism.

In such embodiments, the stabilizing element is a winged bullet-type shape of the port. The winged bullet-type shape is configured to stabilize the port from rolling about a central axis of the port in vivo, thereby maintaining needle access to the septum.

In such embodiments, the stabilizing element is an inflatable section of the port, a pair of legs, a winged bullet-type shape of the port, or a combination thereof. The inflatable section includes an uninflated state imparting a profile to the port configured for subcutaneously tunneling the port from an incision site to an implantation site for the port. The inflatable section further includes an inflated state configured to stabilize the port from rolling about a central axis of the port in vivo, thereby maintaining needle access to the septum. Each of the pair of legs and the winged bullet-type shape is also configured to stabilize the port from rolling about a central axis of the port in vivo, thereby further maintaining needle access to the septum.

In such embodiments, the system further includes an installation tool. The installation tool is configured to hold at least a distal end portion of the port for connecting a catheter to a proximal end portion of the port. The installation tool is further configured to facilitate installing the port in the adapter in the distal end portion of the port tunneler.

Also provided herein is port tunneler including, in some embodiments, an adapter and a release mechanism. The adapter is in a distal end portion of the port tunneler. The adapter is configured to securely hold a streamlined port while subcutaneously tunneling the port from an incision site to an implantation site for the port. The release mechanism is configured to release a streamlined port from the adapter at an implantation site for the port.

In such embodiments, the port tunneler further includes an inflation lumen. The inflation lumen is configured to fluidly connect to an inflatable section of a streamlined port for inflating the inflatable section with one or more fluids.

In such embodiments, the port tunneler further includes a hub at a proximal end of the port tunneler. The hub is configured to fluidly connect with a syringe for delivering one or more fluids to the inflation lumen.

In such embodiments, the adapter is further configured to hold at least a pair of legs of a streamlined port in a collapsed state of the pair of legs.

In such embodiments, the adapter is further configured to hold a streamlined port having a winged bullet-type shape.

In such embodiments, the port tunneler further includes a handle at a proximal end portion of the port tunneler. The handle includes a release button of the release mechanism configured to release a streamlined port from the adapter when the release button is pushed.

In such embodiments, the port tunneler is configured for disposal in a sheath alongside a catheter connected to a streamlined port when the port is disposed in the adapter.

Also provided herein is a streamlined port including, in some embodiments, a septum and a stabilizing element. The septum is disposed over a cavity in a body of the port, and the septum is configured to accept a needle therethrough. The stabilizing element is configured to stabilize the port in vivo and maintain needle access to the septum. The port further includes a profile configured for subcutaneously tunneling the port on a port tunneler from an incision site to an implantation site for the port.

In such embodiments, the stabilizing element is an inflatable section of the port. The inflatable section includes an uninflated state contributing to the profile configured for subcutaneously tunneling the port from an incision site to an implantation site for the port. The inflatable section further includes an inflated state configured to stabilize the port from rolling about a central axis of the port in vivo, thereby maintaining needle access to the septum.

In such embodiments, the inflatable section imparts a triangular prismatic-type shape to at least a portion of the port when in the inflated state. A transverse cross section of such a triangular prismatic-type shape is a triangle.

In such embodiments, the port further includes a one-way valve configured to close off the inflation section upon releasing the port from a port tunneler.

In such embodiments, the stabilizing element is at least a pair of legs. The pair of legs is configured to stabilize the port from rolling about a central axis of the port in vivo, thereby maintaining needle access to the septum.

In such embodiments, the stabilizing element is a winged bullet-type shape of the port. The winged bullet-type shape is configured to stabilize the port from rolling about a central axis of the port in vivo, thereby maintaining needle access to the septum.

Also provided herein is a method including, in some embodiments, loading a streamlined port onto an adapter in a distal end portion of a port tunneler, inserting the port into an incision at a first body location, subcutaneously tunneling the port to an implantation site at a second body location using a tip of the port, and releasing the port from the adapter with a release mechanism of the port tunneler. The adapter of the port tunneler is configured to retain a stabilizing element of the port in a collapsed state. Releasing the port from the adapter allows the stabilizing element of the port to assume an expanded state for stabilizing the port and maintaining needle access to a septum of the port in vivo.

In such embodiments, the method further includes making the incision at the first body location, wherein the incision is sized to require no more than one or two sutures for closing the incision.

In such embodiments, the method further includes implanting a heart end of a catheter in the superior vena cava.

In such embodiments, the method further includes connecting a port end of the catheter to the port and locking the catheter on the port with a catheter lock before loading the port on the adapter of the port tunneler. Connecting and locking the port end of the catheter on the port is either prior to or subsequent to implanting the heart end of the catheter in the superior vena cava.

In such embodiments, the method further includes removing the port from the second body location with a port retriever. The port retriever includes a hook to pull the port out of the second body location by a hole in the tip of the port.

In such embodiments, the method further includes removing the port from the second body location with one or more standard surgical tools.

Also provided herein is a method including, in some embodiments, loading a streamlined port into a proximal end of a sheath, tunneling the port to an implantation site at a second body location at a distal end of the sheath, and releasing the port from the distal end of the sheath. The sheath is configured to retain a stabilizing element of the port in a collapsed state along a length of the sheath. Releasing the port from the sheath allows the stabilizing element of the port to assume an expanded state for stabilizing the port and maintaining needle access to a septum of the port in vivo.

In such embodiments, the method further includes making an incision at a first body location, establishing a tract to the second body location, and sequentially dilating the tract with a sequential dilator set. The incision is sized to require no more than one or two sutures for closing the incision. Subsequent to dilation with the dilator set, the sheath is left in place for the loading of the streamlined port.

In such embodiments, the method further includes implanting a heart end of a catheter in the superior vena cava.

In such embodiments, the method further includes connecting a port end of the catheter to the port and locking the catheter on the port with a catheter lock before loading the streamlined port into the sheath. Connecting and locking the port end of the catheter on the port is either prior to or subsequent to implanting the heart end of the catheter in the superior vena cava.

In such embodiments, the method further includes removing the port from the second body location with a port retriever. The port retriever includes a hook to pull the port out of the second body location by a hole in the tip of the port.

In such embodiments, the method further includes removing the port from the second body location with one or more standard surgical tools.

In such embodiments, the method further includes removing the port from the second body location with another sheath along the tract from the first body location to the second body location.

These and other features of the concepts provided herein may be better understood with reference to the drawings, description, and appended claims.

DRAWINGS

FIG. 1 provides a schematic illustrating a system including a streamlined port and a port tunneler in accordance with some embodiments.

Figure 2:
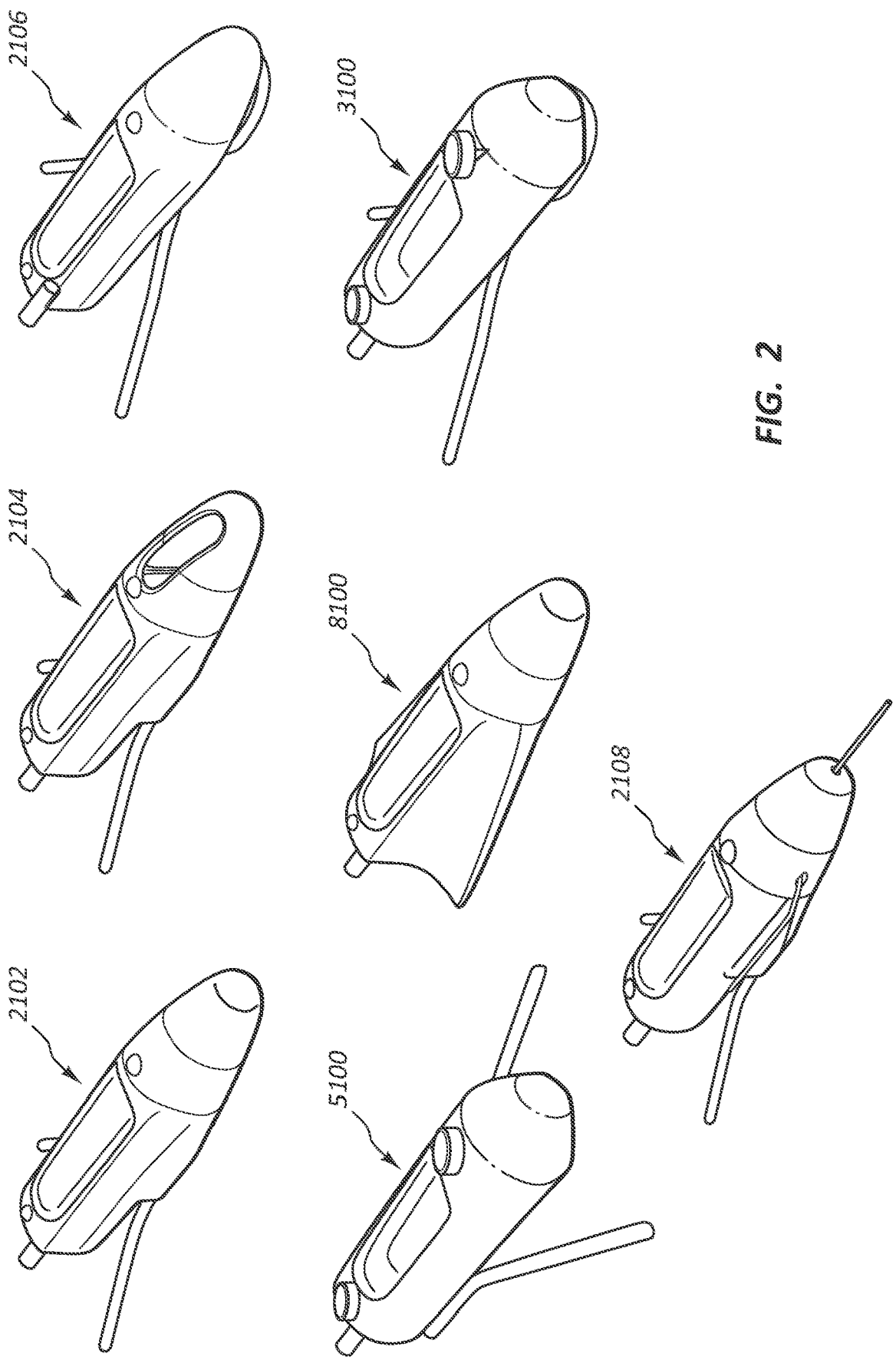

FIG. 2 provides a schematic illustrating a number of streamlined ports in accordance with various embodiments.

FIG. 3A provides a schematic illustrating an end view of a streamlined port including a first pair of legs in accordance with some embodiments.

FIG. 3B provides a schematic illustrating a side view of the streamlined port including the first pair of legs in accordance with some embodiments.

Figure 3D:
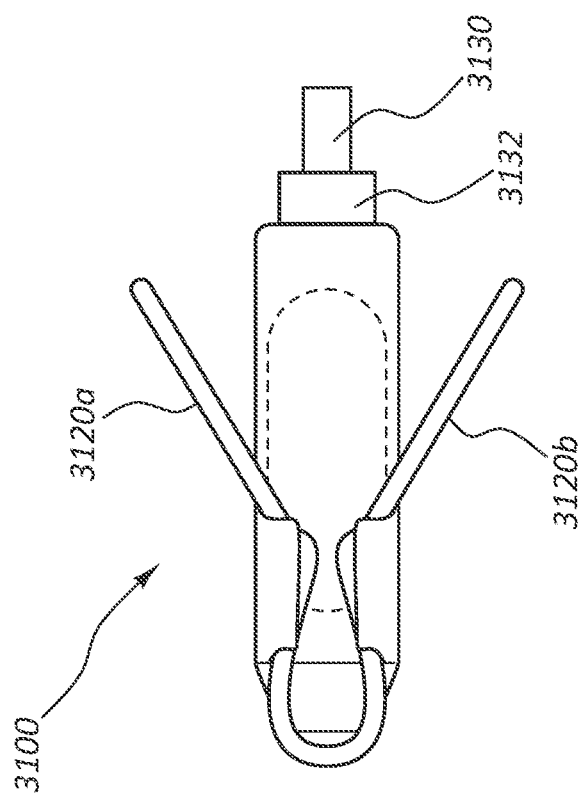
Figure 3C:
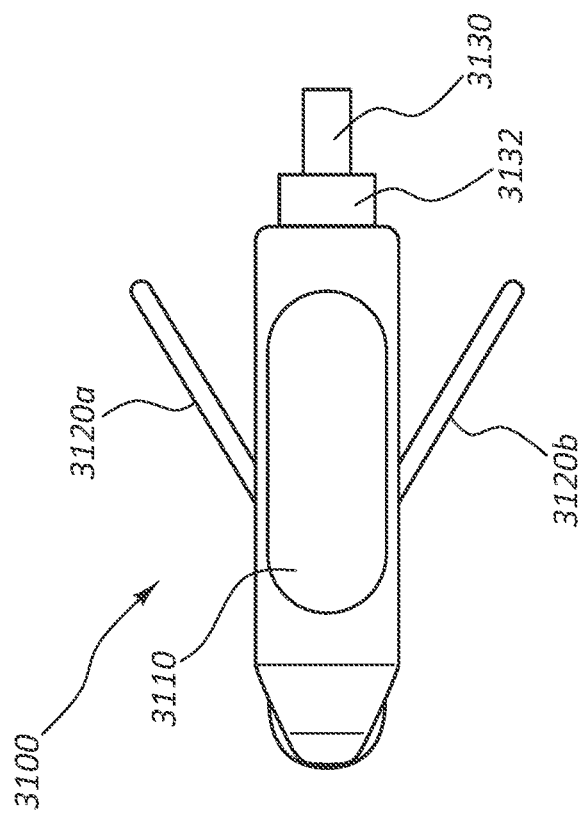

FIG. 3C provides a schematic illustrating a top view of the streamlined port including the first pair of legs in accordance with some embodiments.

FIG. 3D provides a schematic illustrating a bottom view of the streamlined port including the first pair of legs in accordance with some embodiments.

Figure 4:
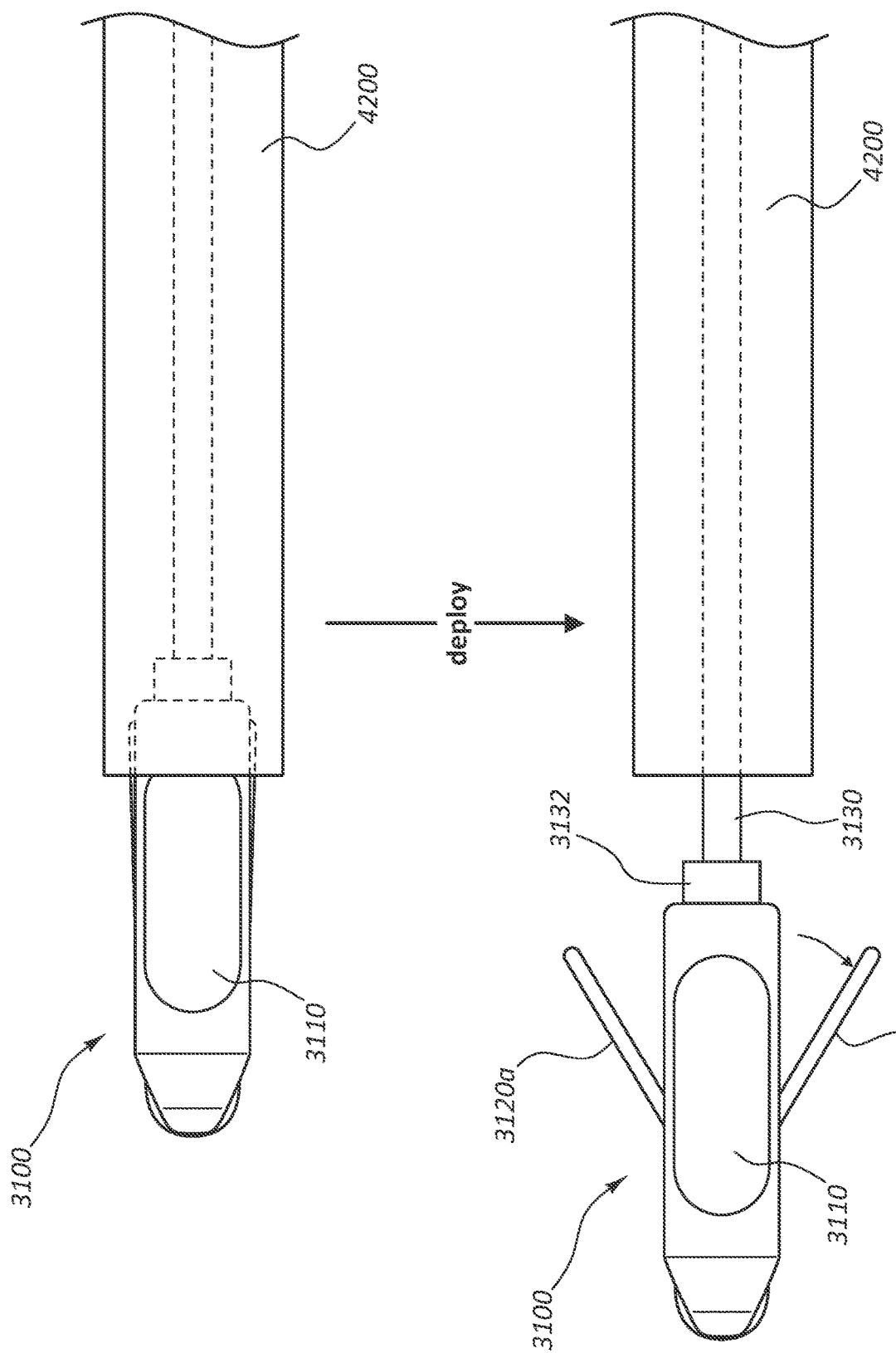

FIG. 4 provides a schematic illustrating deployment of the streamlined port having the first pair of legs from a port tunneler in accordance with some embodiments.

FIG. 5A provides a schematic illustrating an end view of a streamlined port including a second pair of legs in accordance with some embodiments.

FIG. 5B provides a schematic illustrating a side view of the streamlined port including the second pair of legs in accordance with some embodiments.

FIG. 5C provides a schematic illustrating a top view of the streamlined port including the second pair of legs in accordance with some embodiments.

FIG. 6A provides a schematic illustrating an end view of a streamlined port including a third pair of legs in accordance with some embodiments.

FIG. 6B provides a schematic illustrating a side view of the streamlined port including the third pair of legs in accordance with some embodiments.

FIG. 6C provides a schematic illustrating a top view of the streamlined port including the third pair of legs in accordance with some embodiments.

Figure 7:
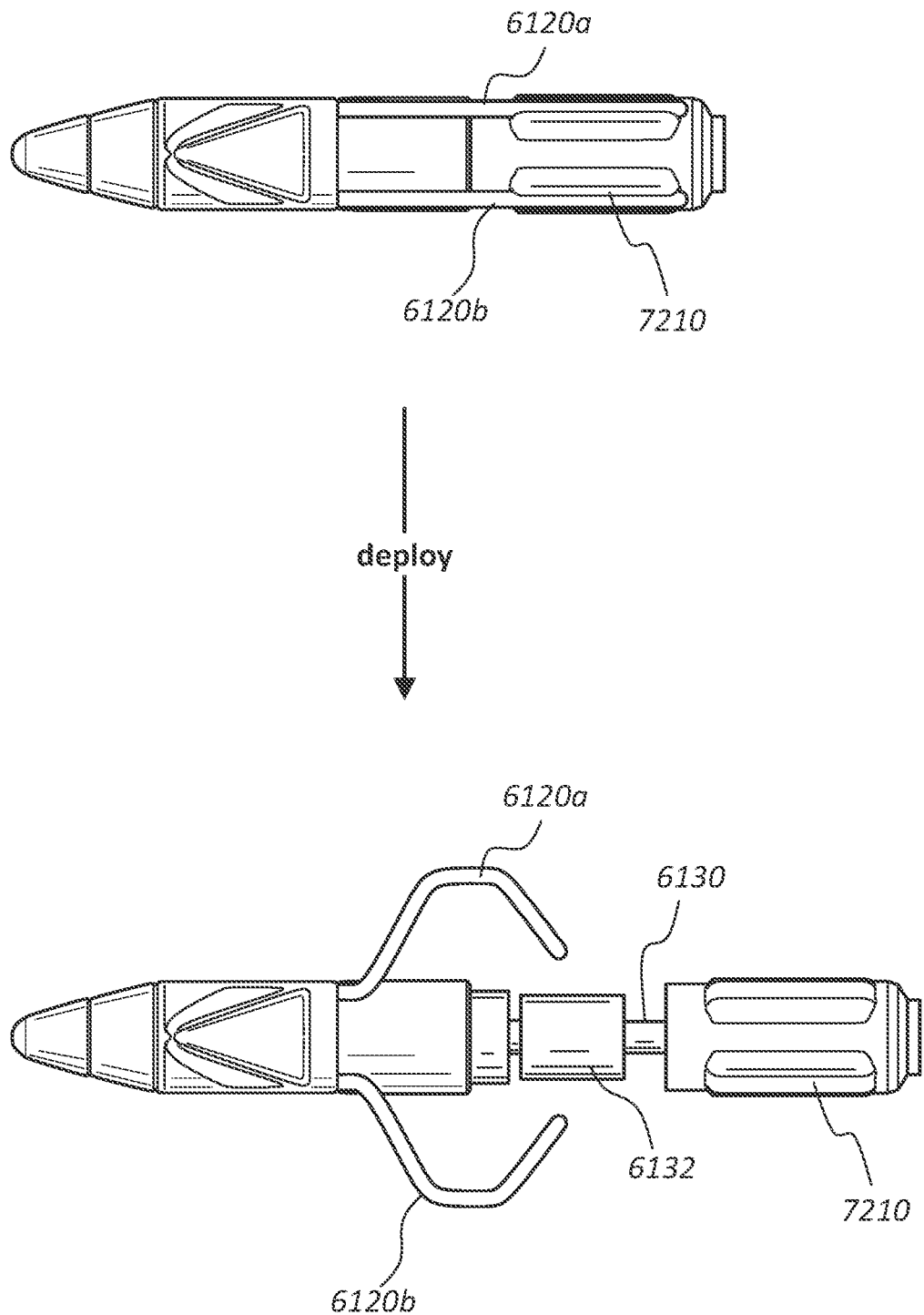

FIG. 7 provides a schematic illustrating deployment of the streamlined port having the second pair of legs from a port tunneler in accordance with some embodiments.

Figure 8C:
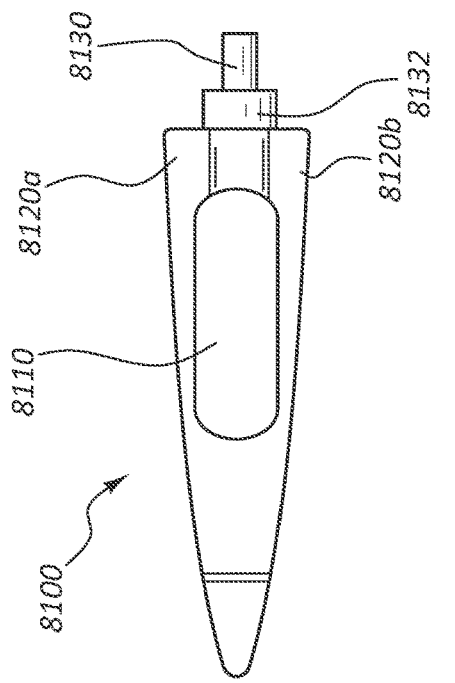
Figure 8B:
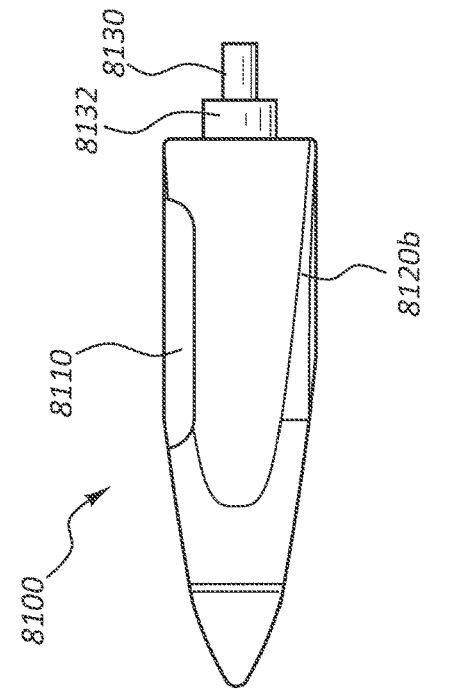
Figure 8A:
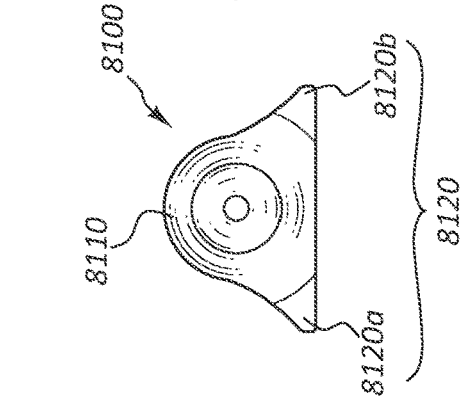

FIG. 8A provides a schematic illustrating an end view of a streamlined port including a winged bullet-type shape in accordance with some embodiments.

FIG. 8B provides a schematic illustrating a side view of the streamlined port including the winged bullet-type shape in accordance with some embodiments.

FIG. 8C provides a schematic illustrating a top view of the streamlined port including the winged bullet-type shape in accordance with some embodiments.

FIG. 9A provides a schematic illustrating an end view of a streamlined port including an inflatable section in accordance with some embodiments.

FIG. 9B provides a schematic illustrating a side view of the streamlined port including the inflatable section in accordance with some embodiments.

Figure 10:
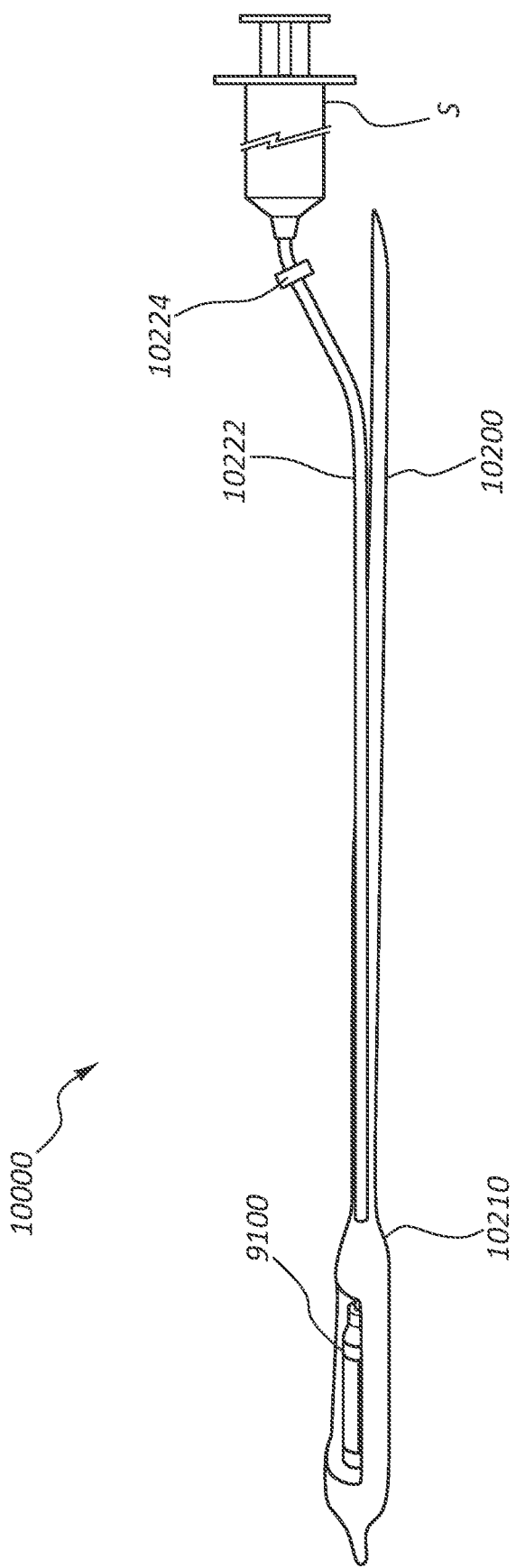

FIG. 10 provides a schematic illustrating a system including the streamlined port of FIGS. 9A and 9B and a port tunneler in accordance with some embodiments.

Figure 11:
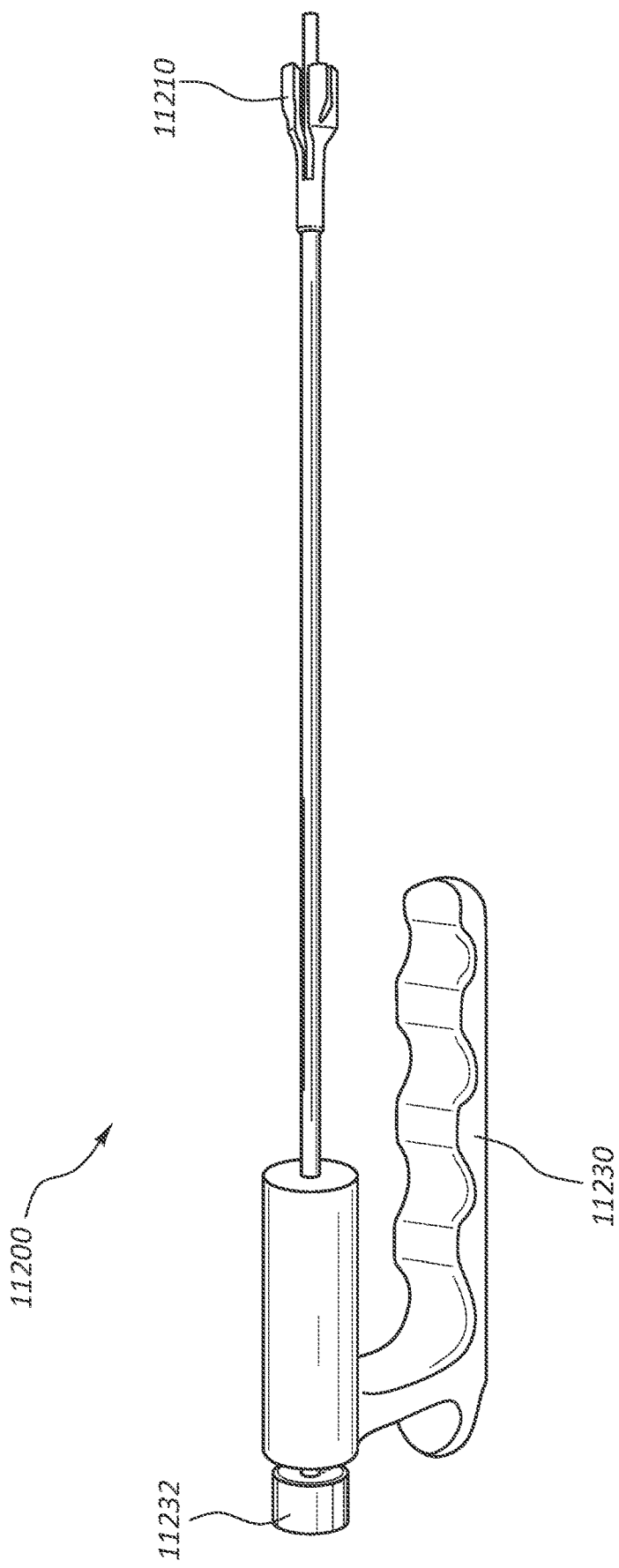

FIG. 11 provides a schematic illustrating a port tunneler including a handle in accordance with some embodiments.

Figure 12:
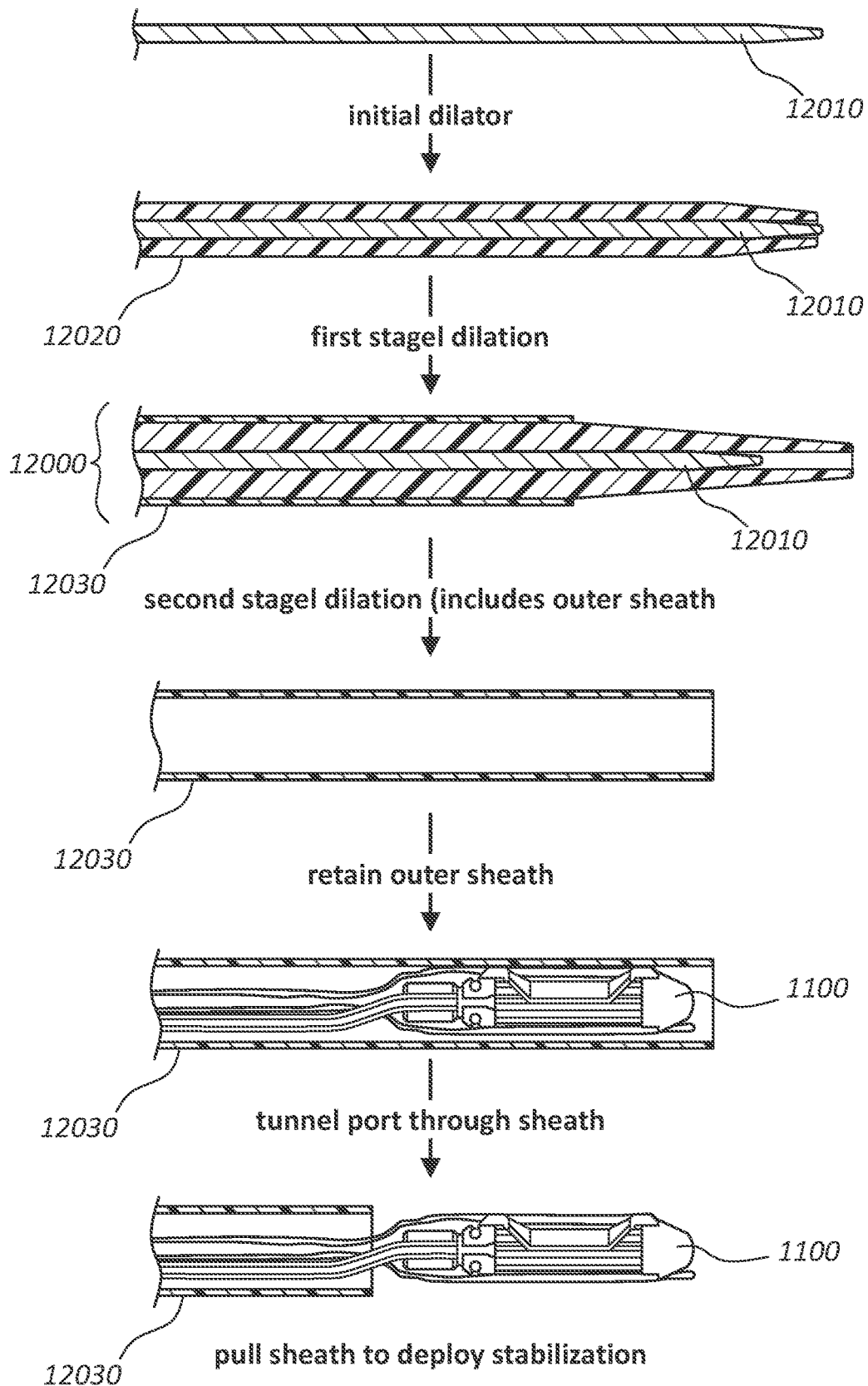

FIG. 12 provides a schematic illustrating a sequential dilator set for a tunneling implant procedure in accordance with some embodiments.

Figure 13:
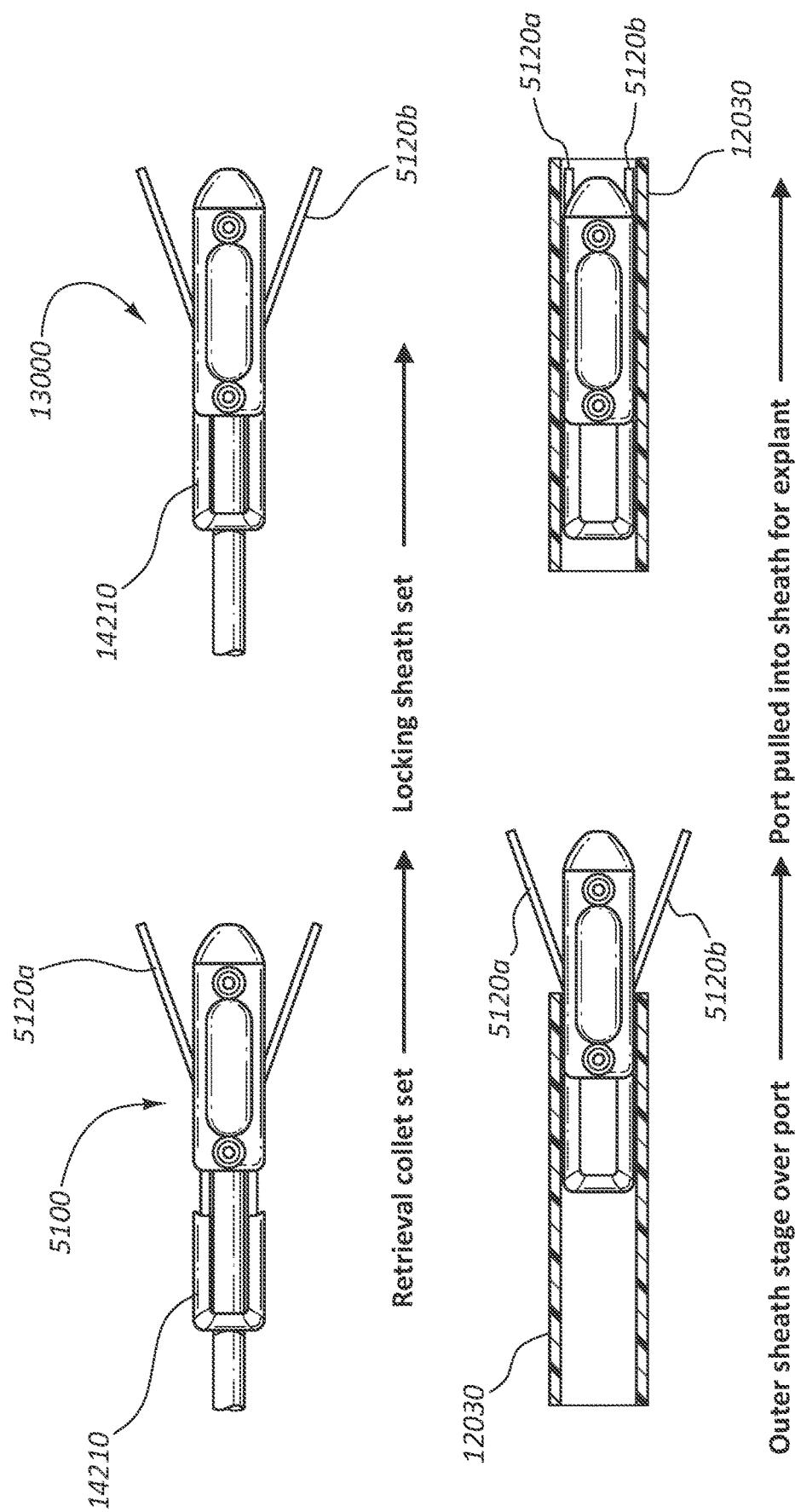

FIG. 13 provides a schematic illustrating a pulling explant procedure with a port retriever in accordance with some embodiments.

Figure 14:
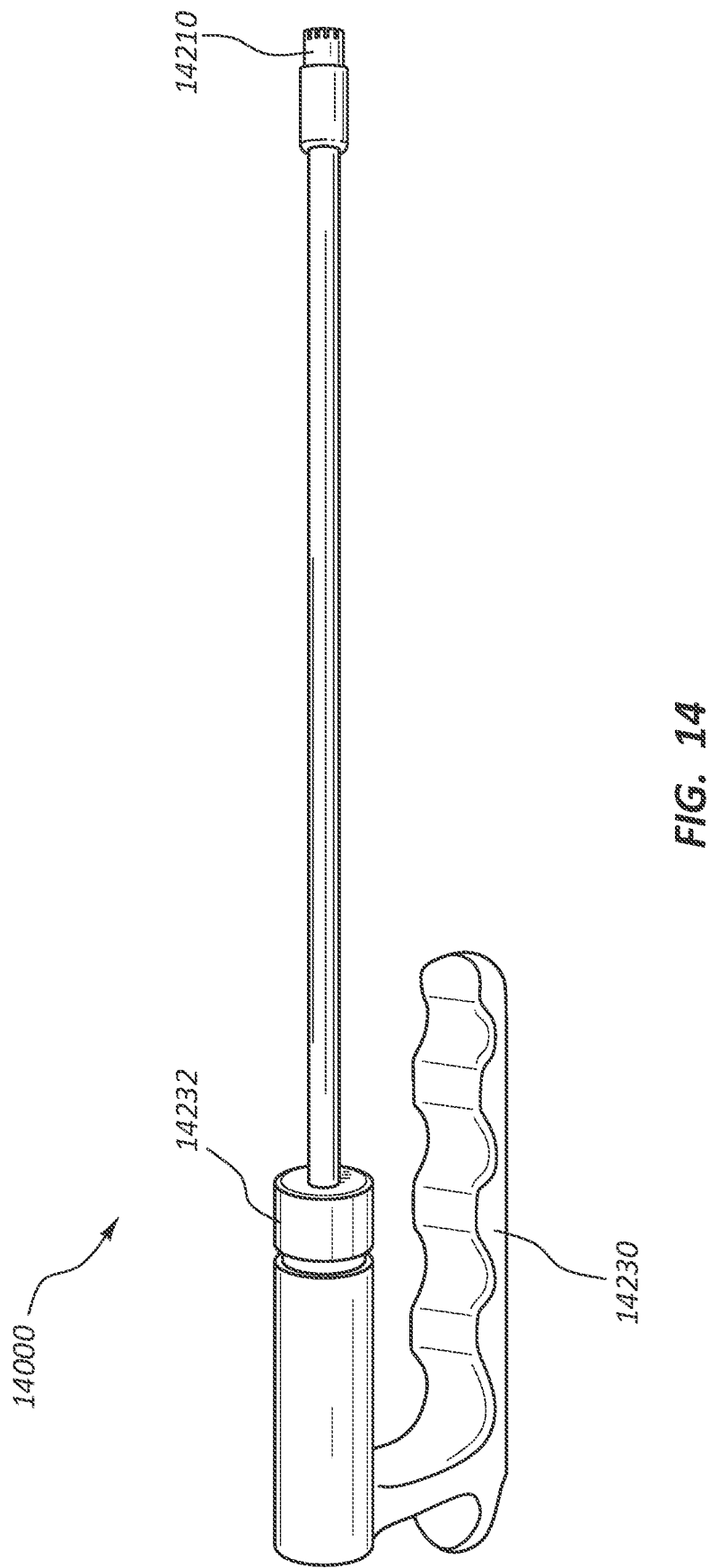

FIG. 14 provides a schematic illustrating a port retriever including a collet in accordance with some embodiments.

Figure 15A:
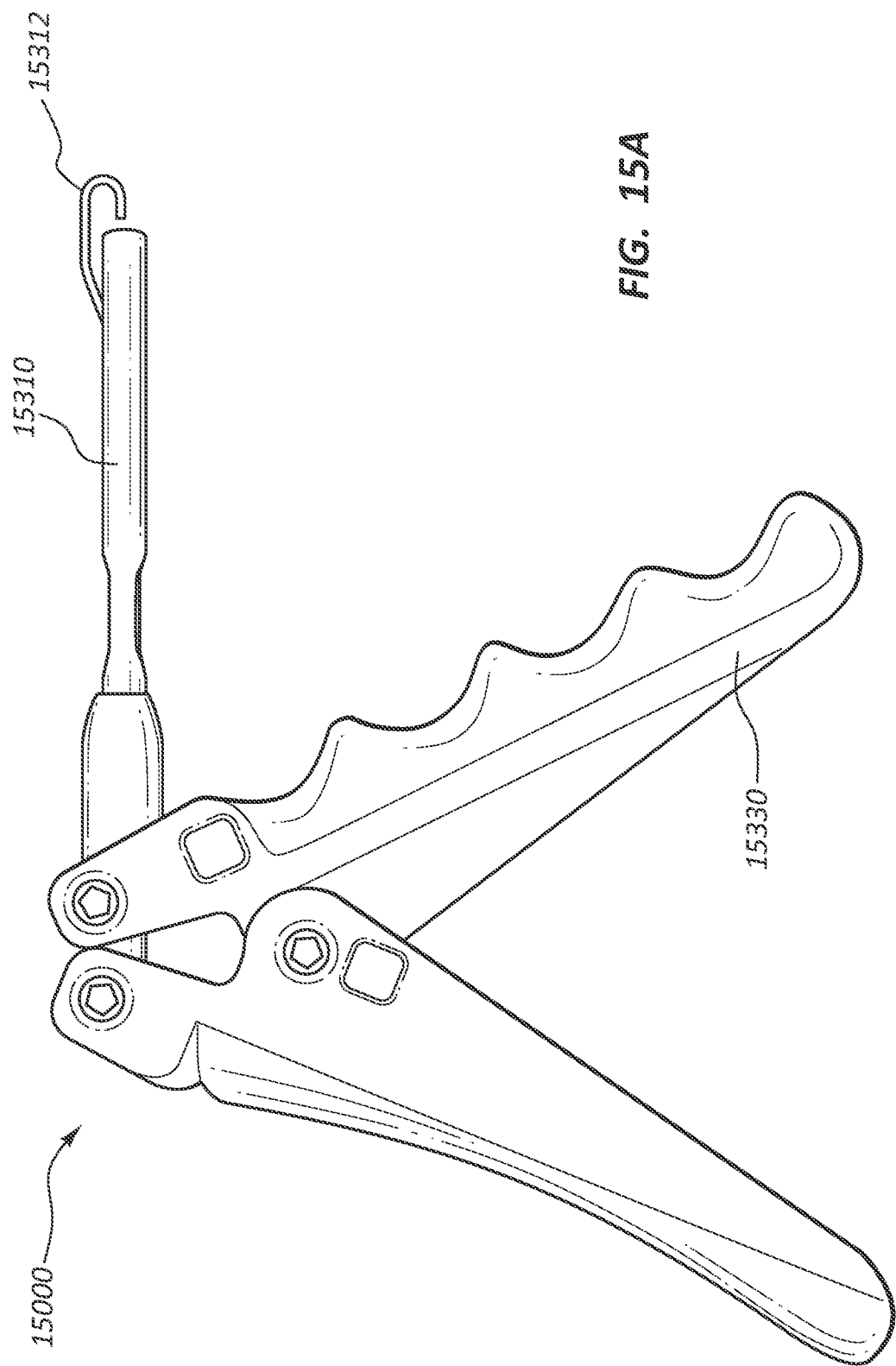

FIG. 15A provides a schematic illustrating a port retriever in a retrieving state in accordance with some embodiments.

Figure 15B:
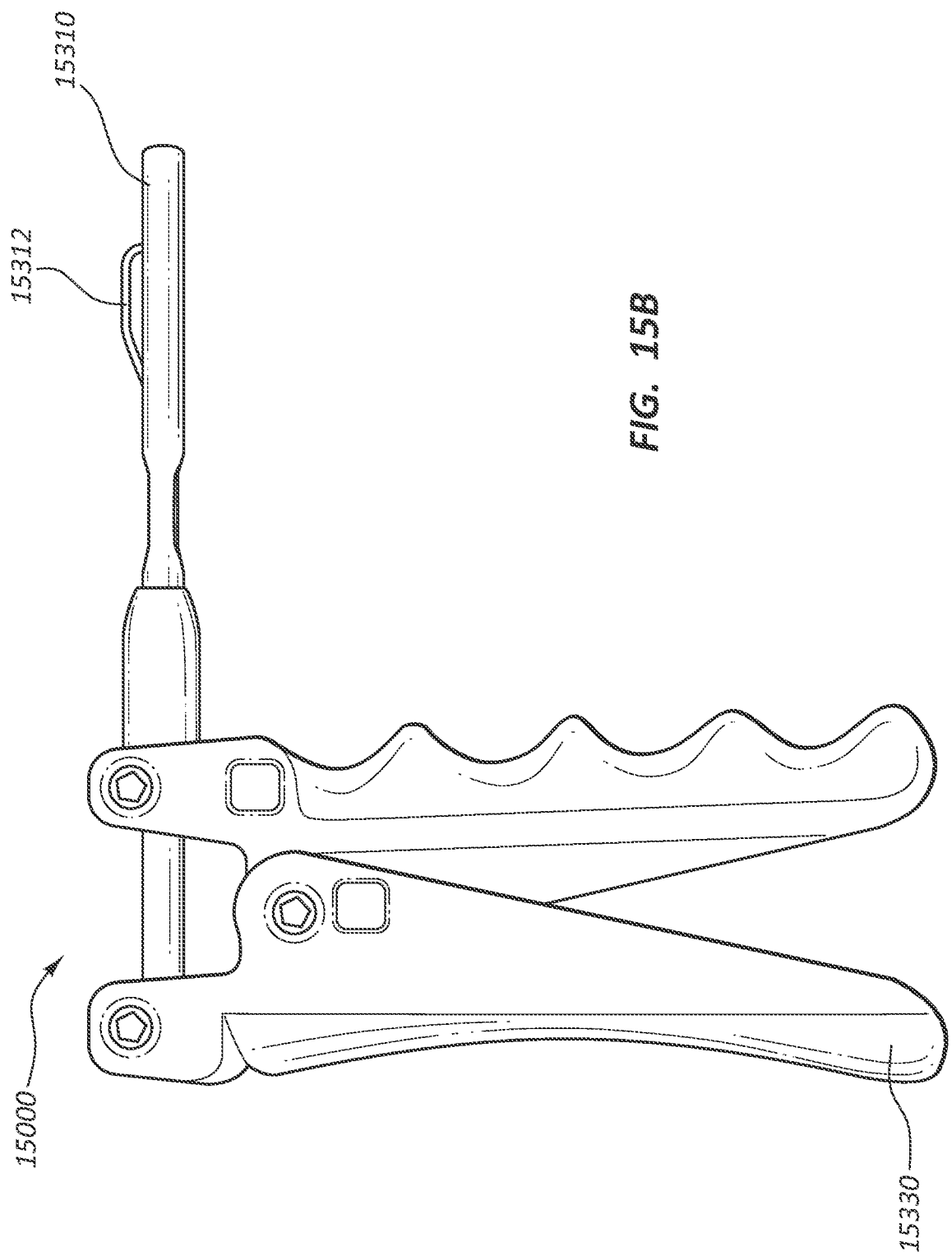

FIG. 15B provides a schematic illustrating a port retriever in a withdrawing state in accordance with some embodiments.

Figure 16:
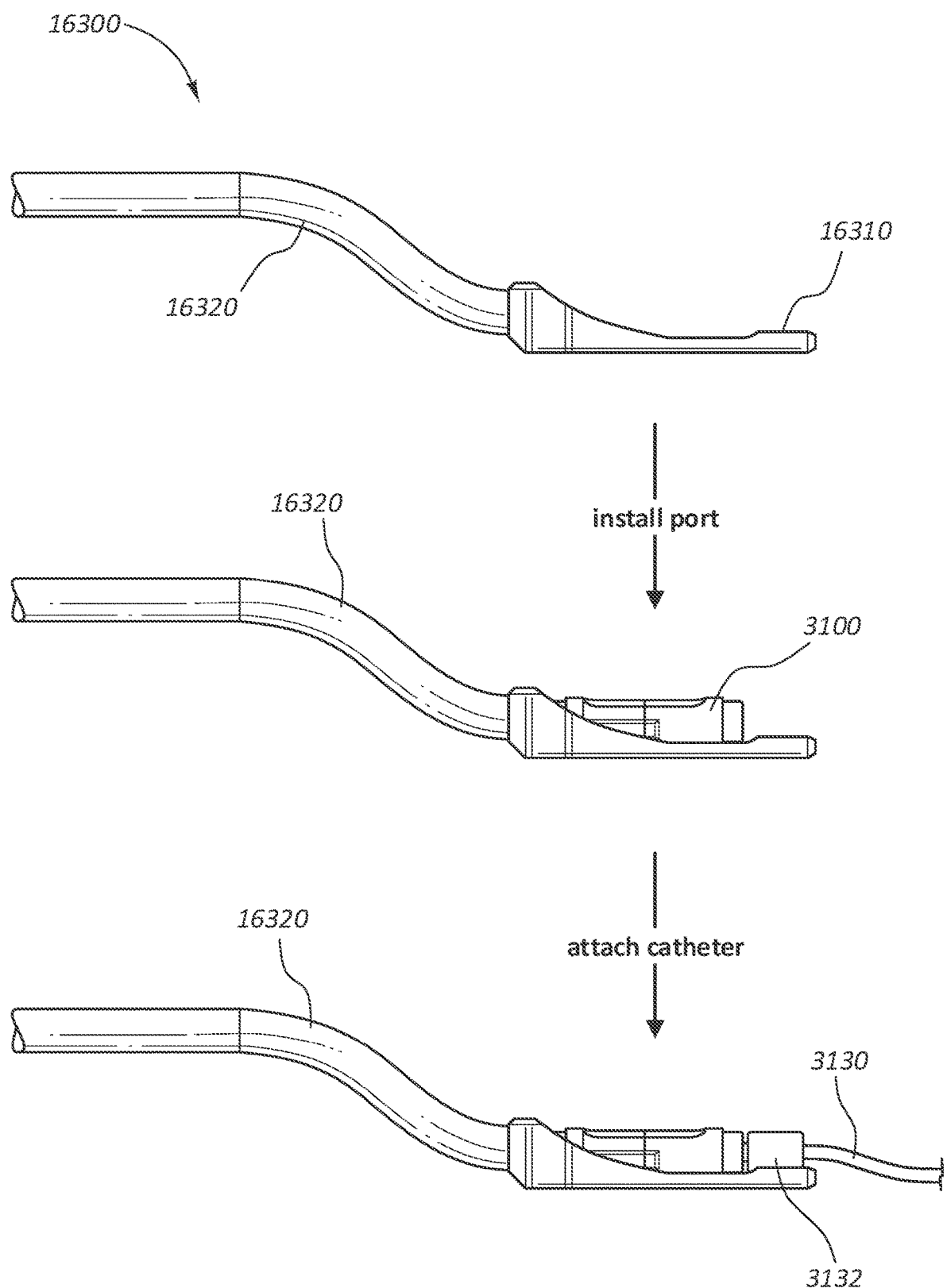

FIG. 16 provides a schematic illustrating an installation tool in accordance with some embodiments.

DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

With respect to "proximal," a "proximal portion" or a "proximal end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

As used herein, a "streamlined port" includes a contour or profile configured to minimize resistance when the port is moved within a patient's body from one location to another, for example when the port is subcutaneously tunneled under a patient's skin from an access site to a final destination separated from the access site. A contour or profile of the streamlined port described herein includes, but is not limited to, the shape of a bullet, pill, or wedge, and is generally longer than it is wide. In some embodiments, a tip of the streamlined port described herein is tapered toward the distal end in order to facilitate direct tunneling of the port from one location to another location through loose connective tissue or subcutaneous tissue. In some embodiments, the tip of the streamlined port is rounded for tunneling the port from one location to another location through a sheath.

Unless defined otherwise, all technical and scientific terms used herein have the same meaning as commonly understood by those of ordinary skill in the art.

Standard procedure for placing a vascular access device such as a port requires two incisions: a first incision near the clavicle, used to introduce a catheter to the superior vena cava for vascular access, and a second incision lower on the chest, where the port is ultimately implanted in a port pocket and connected to the catheter. Creation and closure of the port pocket accounts for a large percentage (about 42%) of the procedure and increases tissue trauma and risk of infection at the site of the second incision. Furthermore, the requirement for the second incision increases potential for scarring.

Provided herein are port tunneling systems and methods that address the foregoing. The port tunneling systems include, in some embodiments, streamlined ports configured for introduction at a first incision site; port delivery systems or "port tunnelers" configured for subcutaneously tunneling the ports to a second implantation site; and port retrieval systems or "port retrievers" configured for retrieving the ports from the second implantation site through the first incision site. Such port tunneling systems and methods for placing the ports thereof removes a need of a second incision for creating a port pocket and implanting a port therein. This decreases procedure time for port placement, mitigates tissue trauma, and reduces risk of infection at the second site. In addition, removal of the second incision has a cosmetic benefit for the patient in terms of less scarring.

Referring now to FIG. 1, a schematic is provided illustrating a port tunneling system 1000 including a streamlined port 1100 and a port tunneler 1200 in accordance with some embodiments. Before addressing specific features of any port tunneling system or components thereof (e.g., streamlined ports, port tunnelers, port retrievers, installation tools, etc.), some general features of the port tunneling systems are addressed using the port tunneling system 1000 of FIG. 1, thereby providing a general explanation of the concepts provided herein. As such, it is possible some of the port tunneling systems do not include one or more of the general features. Port retrievers and installation tools, which are also part of the port tunneling systems, are addressed later.

A streamlined port, such as the streamlined port 1100, is a percutaneous port including a septum and a stabilizing element for stabilizing the port in vivo. (See, for example, septa 3110, 5110, 6110, and 8110 and stabilizing elements 3120, 5120, 6120, and 8120 of FIGS. 3A-3D, 5A-5C, 6A-6C, 8A-8C.) The septum is disposed over a chambered cavity in a body of the port, and the septum is configured to accept a needle through the septum, thereby providing needle access to one or more chambers of the cavity. The stabilizing element is expandable or static, and the stabilizing element is configured to stabilize the port in vivo and maintain needle access to the septum and the one or more chambers of the port. In addition, the port includes a sufficiently small profile for subcutaneously tunneling the port on a port tunneler from an incision site to an implantation site (e.g., upper chest) for the port. The small profile resembles a bullet, pill, or wedge in shape depending upon the particular embodiment, but the port is generally longer than it is wide.

A port tunneler such as the port tunneler 1200 includes an adapter such as adapter 1210 and a release mechanism for releasing the streamlined port from the adapter. (See, for example, adapter 7210 of FIG. 7.) The adapter is at a distal end portion of the port tunneler or a distal end thereof. The adapter is configured to securely hold the port while subcutaneously tunneling the port from an incision site to an implantation site for the port. The release mechanism is configured to release the port from the adapter at the implantation site for the port.

A port tunneler such as the port tunneler 1200 can be configured for disposal in a sheath along with a catheter such as catheter 1130 connected to a streamlined port such as the streamlined port 1100 as shown in FIG. 1. Releasing the port from the adapter via the release mechanism of the port tunneler frees the catheter to slide out of the sheath as the port tunneler is withdrawn from a patient, ultimately through the incision site of the patient. The sheath can be a pull-apart sheath configured for extraction of the catheter through the sheath when the sheath is pulled apart. This is useful when an end of the catheter opposite the port is placed in, for example, the superior vena cava, before subcutaneously tunneling the port to the implantation site. However, the catheter can be placed either before or after subcutaneously tunneling the port to the implantation site. In addition, a sheath need not be used, as a guidewire in place can be directly followed by the port tunneler 1200 with the streamlined port 1100 and catheter 1130 loaded thereon.

A port tunneler such as the port tunneler 1200 can also include a handle such as handle 1230 at a proximal end portion of the port tunneler or a proximal end thereof. (See also FIGS. 11A and 11B.) The handle includes a release (e.g., release button 1232, trigger, switch, etc.) of the release mechanism configured to release a streamlined port such as the streamlined port 1100 from the adapter when the release is engaged. As shown in FIG. 1, for example, the handle 1230 includes the release button 1232, which is configured to push a deployment rod of the release mechanism to disengage the port from the adapter when the release button is pushed.

Having addressed some general features of the port tunneling systems, some specific features of the port tunneling systems are now addressed, such as specific features of streamlined ports, port tunnelers, port retrievers, and installation tools. However, it should be understood that a particular embodiment such as, but not limited to, any one of the streamlined ports of FIG. 2 can have features that can be readily separated from the particular embodiment and optionally combined with or substituted for features of any of a number of the other embodiments.

Referring now to FIG. 2, a schematic is provided illustrating a number of streamlined ports in accordance with various embodiments. As shown, the number of ports includes ports 2102, 2104, 2106, 2108, 3100, 5100, and 8100.

Each streamlined port is configured for insertion through a puncture at a location such as the internal jugular access site and deployment at an implantation site by subcutaneously tunneling the port through, for example, the upper chest. Thus, each port includes a profile configured for using the port as a leading edge of a port tunneler, delivering the port through an introducer sheath, or both. A tunneling tip of a port body can be configured as aggressive for direct tunneling on a port tunneler or over a wire, or the tunneling tip can be configured as mild for delivery through an introducer sheath.

Each streamlined port also includes at least one expandable or static stabilizing element configured to provide stability to the port in vivo (e.g., in a port pocket at the implantation site). Such stabilizing elements include, but are not limited to, one or more stabilizing elements selected from legs (or wires), wings, inflatable elements, and shapes of the ports themselves, at least the legs and inflatable elements being deployable after establishing the port pocket for implantation. Furthermore, the legs can be an open cell design, which allows a port to be pulled out of connective tissue during an explant procedure without tearing the tissue. Such stabilizing elements are configured to stabilize their respective ports by preventing the ports from rolling about their central axes in vivo. For example, a port can include deployable legs such as the port 2102, 2104, 2106, 3100, or 5100, or the port can include wings such the port 8100.

Such stabilizing elements are configured for different implant and explant procedures with different tools, some of which tools are standard surgical tools (e.g., clamps, pliers, etc.), and some of which tools are included in the port tunneling systems such as port retrievers configured to engage with hooks, holes, or undercuts in the streamlined ports. For example, a port with deployable legs opening toward a proximal end or away from the tunneling tip of the port (e.g., ports 2102, 2104, and 2106) is configured for implantation using a port tunneler or sequential dilator set through an incision at the internal jugular access site. Port 2108, which also has deployable legs opening toward a proximal end of the port, is configured for delivery over a wire as shown by the wire entering the tip of the port 2108 and exiting through a side of the tip. Explantation of such ports is accomplished using a port retriever (e.g., the port retriever 1500 of FIGS. 15A and 15B for the port 2104) or a sheath through a second incision in the upper chest. In another example, a port with deployable legs opening away from a proximal end or toward the tunneling tip of the port (e.g., port 5100) is configured for implantation and explantation using at least the sequential dilator set through a single incision at the internal jugular access site.

In view of the foregoing, the streamlined port 2102 is configured for a tunneling implant procedure through a first incision at, for example, the internal jugular access site and a pulling explant procedure through a second incision in, for example, in the upper chest, which explant procedure does not require retracting the stabilizing pair of legs. The streamlined port 2104 is likewise configured for a tunneling implant procedure through the first incision, but the port 2104 is further configured for a sheath-assisted explant procedure in which the stabilizing pair of legs are retracted with a hook of a port retriever (e.g., the port retriever 1500 of FIGS. 15A and 15B) for pulling the port through the sheath. Each port of the streamlined ports 2106 and 3100 includes a retractable stabilizing element (see, for example, FIG. 3D), the stabilizing element being a pair of legs when extended. The port 3100 is configured with a milder tip for a sheath-assisted implant procedure, and the port 2106 is configured with a more aggressive tip for a tunneling implant procedure. The streamlined port 5100 is configured with a milder tip for a sheath-assisted implant procedure through an incision at, for example, the internal jugular access site and an explant procedure through the same internal jugular access site. The streamlined port 8100 is configured for a tunneling implant procedure and an explant procedure with standard surgical clamps or pliers like the port 2102; that is, the ports 2102 and 8100 need not the port retrievers provided herein for explant. As such, ports can be configured with any combination of a number of features selected from a mild tip for a sheath-assisted implantation procedure or an aggressive tip for a tunneling (including over a wire) implantation procedure; one or more stabilizing elements such as legs (or wires), wings, and shapes of the ports themselves; directionality of the one or more stabilizing elements for implantation and explantation through a single incision or two different incisions; and additional features such as hooks, holes, or undercuts for retrieval with one or more port retrievers (e.g., the port retriever 1500 of FIGS. 15A and 15B). The ports of FIG. 2 are examples illustrating such different combinations.

Each streamlined port includes a septum having a shape and configuration comparable to existing non-streamlined ports. For example, the septum has a surface area commensurate with existing non-streamlined ports. In contrast to existing non-streamlined ports, any port-identifying bumps (e.g., power port-identifying bumps for streamlined power ports) or septum-indicating bumps are on the port body, which maximizes septum surface area for needle access. However, such port-identifying bumps and septum-indicating bumps are not limited to placement on the port body. The port-identifying bumps and septum-indicating bumps can be included on septa in some embodiments.

Each streamlined port can be radiopaque, MRI conditional or safe, or a combination thereof.

Each streamlined port can further include a radio-frequency identification ("RFID") tag. The RFID tag of a port can include readable information written to the RFID tag at the time of manufacturing the port. The readable information can identify the type of port by its model number, lot number, date of manufacturing, etc. Furthermore, the RFID tag of a port can be writable such that patient information can be written to the RFID tag.

Each streamlined port can be press fit, welded, bonded or threaded together, or printed using metal 3D printing to form the port body. The septum is symmetrical, and the septum can be mounted by various pressure installation fixtures optionally with additional adhesive or thermal bonding. Stabilization elements such as stabilizing pair of legs (or wires) can be fixed to the port body for an implant or explant procedure, or moveable in order to deliver or retract stability for an implant or explant procedure.

Referring now to FIGS. 3A-3D, schematics are provided illustrating views of a streamlined port 3100 including a first pair of legs 3120 in accordance with some embodiments. As shown, the port 3100 includes a septum 3110 and the first pair of legs 3120. The first pair of legs 3120 includes a first leg 3120a and a second leg 3120b. A catheter 3130 connected to the port 3100 with a catheter lock 3132 is also shown in at least FIGS. 3B and 3C. The port 3100 includes a retractable stabilizing element, the stabilizing element being the first pair of legs 3120 when extended. The port 3100 is configured for at least a sheath-assisted implant procedure.

The septum 3110 of the streamlined port 3100 is opposite the first pair of legs 3120; however, the septum 3110 can be uniquely placed in a distal end of the port 3100 as exemplified by the port 1200 of FIGS. 9A and 9B. Such a unique placement of the septum 3110 in the distal end of the port 3100 is an outgrowth of the port 3100 needing only a single incision for introducing, tunneling, and placing the port 3100 at an implantation site. Eliminating the second incision commonly used to place a port reduces trauma, risk of infection, and scarring at the site of the would-be second incision, thereby freeing the area for injections through the uniquely placed septum 3110 in the distal end of the port 3100.

The first pair of legs 3120 of the streamlined port 3100 is an example of a stabilizing element of the streamlined ports provided herein, the first pair of legs 3120 configured to stabilize the port 3100 from rolling about a central axis of the port 3100 in vivo, thereby maintaining needle access to the septum 3110. The first pair of legs 3120 of the port 3100 is configured to assume a collapsed state while in an adapter of a port tunneler (or introducer sheath) and an expanded or deployed state while outside the adapter of the port tunneler (or the introducer sheath). The expanded state of the first pair of legs 3120 stabilizes the port 3100 from rolling about a central axis of the port 3100 in vivo, thereby maintaining needle access to the septum 3110.

In the collapsed state of the first pair of legs 3120, each leg of the legs 3120*a* and 3120*b* lies along its own side of the body of the streamlined port 3100 and is held in place by the adapter of the port tunneler (or the introducer sheath). The collapsed state of the first pair of legs 3120 allows the port 3100 to assume an initially small profile for subcutaneously tunneling the port 3100 on the port tunneler from an incision site to an implantation site. That is, the first pair of legs 3120 includes a collapsed state imparting or otherwise contributing to a sufficiently small profile of the port 3100 for subcutaneously tunneling the port 3100 from an incision site to an implantation site for the port 3100.

In the expanded state of the first pair of legs 3120, each leg of the legs 3120*a* and 3120*b* is configured via shape memory to jut out from a proximal end of the body of the streamlined port 3100. The expanded state of the first pair of legs 3120 allows the port 3100 to assume a subsequently large profile for fixing the port 3100 at the implantation site and maintaining needle access to the septum 3110. That is, the first pair of legs 3120 includes an expanded state configured to stabilize the port 3100 from rolling about a central axis of the port 3100 in vivo, thereby maintaining needle access to the septum 3110.

The leg 3120*a* and the leg 3120*b* can be joined to form a 'U' shape at a distal end of the streamlined port 3100 as best shown in FIG. 3D. Each leg of the legs 3120*a* and 3120*b* is be held captive by its own leg retainer (e.g., a hole through a body extension of the port 3100), which allows, in some embodiments, the U-shaped pair of legs 3120 to longitudinally slide along the body of the port 3100. Owing to the shape memory of the pair of legs 3120, sliding the U-shaped pair of legs 3120 toward the distal end of the port 3100 shortens the pair of legs proximal to the leg retainers and narrows their tip-to-tip width. Sliding the U-shaped pair of legs 3120 toward a proximal end of the port 3100 lengthens the pair of legs proximal to the leg retainers and widens their tip-to-tip width. This is useful for adjusting the tip-to-tip width of the pair of legs 3120 of the port 3100 for implantation sites of different sizes.

Referring now to FIG. 4, a schematic is provided illustrating deployment of the streamlined port 3100 having the first pair of legs 3120 from a port tunneler 4200 in accordance with some embodiments. During a tunneling implant procedure, the port 3100 and the pair of legs 3120 are contained within the port tunneler 4200 or an adapter in a distal end of the port tunneler 4200. (See, for example, adapter 7210 of FIG. 7.) As such, the port tunneler 4200 restrains the pair of legs 3120 from deployment until the port 3100 exits the port tunneler 4200 at the implantation site (e.g., port pocket) for the port 3100. Upon releasing the port 3100 from the port tunneler 4200 with the release mechanism, the first pair of legs 3120 is configured to assume a deployed state.

Referring now to FIGS. 5A-5C, schematics are provided illustrating views of a streamlined port 5100 including a second pair of legs 5120 in accordance with some embodiments. As shown, the port 5100 includes a septum 5110 and the second pair of legs 5120. The second pair of legs 5120 includes a first leg 5120*a* and a second leg 5120*b*. A catheter 5130 connected to the port 5100 with a catheter lock 5132 is also shown in FIGS. 5B and 5C. The port 5100 is configured with the distally opening second pair of legs 5120 for at least a sheath-assisted implant procedure at the internal jugular access site and an explant procedure through the access site.

The septum 5110 of the streamlined port 5100 is opposite the second pair of legs 5120; however, the septum 5110 can be uniquely placed in a distal end of the port 5100 as exemplified by the port 1100 of FIGS. 9A and 9B. Again, such a unique placement of a septum in a distal end of a streamlined port is an outgrowth of the port needing only a single incision for introducing, tunneling, and placing the port at an implantation site.

The second pair of legs 5120 of the streamlined port 5100 is another example of a stabilizing element of the streamlined ports provided herein, the second pair of legs 5120 configured to stabilize the port 5100 from rolling about a central axis of the port 5100 in vivo, thereby maintaining needle access to the septum 5110. The second pair of legs 5120 of the port 5100 is configured to assume a collapsed state while in an adapter of a port tunneler (or an introducer sheath) and an expanded or deployed state while outside the adapter of the port tunneler (or the introducer sheath). The expanded state of the second pair of legs 5120 stabilizes the port 5100 from rolling about a central axis of the port 5100 in vivo, thereby maintaining needle access to the septum 5110.

In the collapsed state of the second pair of legs 5120, each leg of the legs 5120*a* and 5120*b* lies along its own side of the body of the streamlined port 5100 and is held in place by the adapter of the port tunneler (or the introducer sheath). The collapsed state of the second pair of legs 5120 allows the port 5100 to assume an initially small profile for subcutaneously tunneling the port 5100 on the port tunneler from an incision site to an implantation site. That is, the second pair of legs 5120 includes a collapsed state imparting or otherwise contributing to a sufficiently small profile of the port 5100 for subcutaneously tunneling the port 5100 from an incision site to an implantation site for the port 5100.

In the expanded state of the second pair of legs 5120, each leg of the legs 5120*a* and 5120*b* is configured via shape memory to jut out from a distal end of the body of the streamlined port 5100. The expanded state of the second pair of legs 5120 allows the port 5100 to assume a subsequently large profile for fixing the port 5100 at the implantation site and maintaining needle access to the septum 5110. That is, the second pair of legs 5120 includes an expanded state configured to stabilize the port 5100 from rolling about a central axis of the port 5100 in vivo, thereby maintaining needle access to the septum 5110.

Each leg of the legs 5120*a* and 5120*b* is held captive by its own leg retainer (e.g., a hole through a body extension of the port 5100), which allows, in some embodiments, each leg of the legs 5120*a* and 5120*b* to individually and longitudinally slide along the body of the streamlined port 5100. Owing to the shape memory of each leg of the legs 5120*a* and 5120*b*, sliding a first leg such as the leg 5120*a* toward the proximal end of the port 5100 shortens the leg distal to its leg retainer and narrows a tip-to-tip width with a second leg such as the leg 5120*b*. Sliding the first leg toward a distal end of the port 5100 lengthens the leg distal to the leg retainer and widens the tip-to-tip width with the second leg. Not only is this useful for adjusting the tip-to-tip width of the pair of legs 5120 in the expanded state of the port 5100 for implantation sites of different sizes, but individually adjusting each leg of the legs 5120*a* and 5120*b* allows for fine tuning of the expanded state.

The streamlined ports 3120 and 5120 respectively of FIGS. 3A-3D and 5A-5C differ in at least placement of their leg retainers and joining of their pairs of legs. Again, the port 5100 is configured with the distally opening second pair of legs 5120 for at least a sheath-assisted implant procedure at the internal jugular access site and an explant procedure through the access site. However, the leg retainers on the body of the streamlined port 3120 can be located on the proximal end of the body of the port 3120 (like the port 5120) instead of the distal end of the body. Furthermore, the leg 5120*a* and the leg 5120*b* can be joined to form a 'U' shape (like the first pair of legs 3120 of the port 3120) at the proximal end of the streamlined port 5100 instead of being unjoined or detached. Again, the particular embodiments provided herein are examples and do not limit the scope of the concepts provided herein.

Referring now to FIGS. 6A-6C, schematics are provided illustrating views of a streamlined port 6100 including a third pair of legs 6120 in accordance with some embodiments. As shown, the port 6100 includes a septum 6110 and the third pair of legs 6120. The third pair of legs 6120 includes a first leg 6120*a* and a second leg 6120*b*. A catheter 6130 connected to the port 6100 with a catheter lock 6132 is also shown in FIGS. 6B and 6C.

The septum 6110 of the streamlined port 6100 is opposite the third pair of legs 6120; however, the septum 6110 can be uniquely placed in a distal end of the port 6100 as exemplified by the port 1100 of FIGS. 9A and 9B. Again, such a unique placement of a septum in a distal end of a streamlined port is an outgrowth of the port needing only a single incision for introducing, tunneling, and placing the port at an implantation site.

The third pair of legs 6120 of the streamlined port 6100 is another example of a stabilizing element of the streamlined ports provided herein, the third pair of legs 6120 configured to stabilize the port 6100 from rolling about a central axis of the port 6100 in vivo, thereby maintaining needle access to the septum 6110. The third pair of legs 6120 of the port 6100 is configured to assume a collapsed state while in an adapter of a port tunneler (or an introducer sheath) and an expanded or deployed state while outside the adapter of the port tunneler (or the introducer sheath). The expanded state of the third pair of legs 6120 stabilizes the port 6100 from rolling about a central axis of the port 6100 in vivo, thereby maintaining needle access to the septum 6110.

In the collapsed state of the third pair of legs 6120, each leg of the legs 6120*a* and 6120*b* lies along its own side of the body of the streamlined port 6100 and is held in place by the adapter of the port tunneler (or the introducer sheath). The collapsed state of the third pair of legs 6120 allows the port 6100 to assume an initially small profile for subcutaneously tunneling the port 6100 on the port tunneler from an incision site to an implantation site. That is, the third pair of legs 6120 includes a collapsed state imparting or otherwise contributing to a sufficiently small profile of the port 6100 for subcutaneously tunneling the port 6100 from an incision site to an implantation site for the port 6100.

In the expanded state of the third pair of legs 6120, each leg of the legs 6120*a* and 6120*b* is configured via shape memory to bow in a medial section of the leg and out from a proximal end portion or proximal end of the body of the streamlined port 6100. The expanded state of the third pair of legs 6120 allows the port 6100 to assume a subsequently large profile for fixing the port 6100 at the implantation site and maintaining needle access to the septum 6110. That is, the third pair of legs 6120 includes an expanded state configured to stabilize the port 6100 from rolling about a central axis of the port 6100 in vivo, thereby maintaining needle access to the septum 6110.

Each leg of the legs 6120*a* and 6120*b* is held captive by its own leg retainer (e.g., a hole through a body extension of the port 6100) and fixed to the body of the streamlined port 6100. Owing to the shape memory of each leg of the legs 6120*a* and 6120*b*, immediately upon release of the streamlined port from the adapter of the port tunneler, each leg bows in the medial section of the leg and out from the proximal end portion or proximal end of the body of the port 6100. That being said, the port 6100 can be alternatively configured such that the third pair of legs 6120 bows out from a distal end portion or distal end of the body of the port 6100 akin to the streamlined port 5100 of FIGS. 5A-5C. The bowed medial sections of the pair of legs 6120 form a compressible spring with a spring constant for expanding the port 6100 to fit implantation sites of different sizes in the expanded state. Furthermore, the spring constant is sufficient to fix the port 6100 at an implantation site without causing trauma.

Referring now to FIG. 7, a schematic is provided illustrating deployment of the streamlined port 6100 having the third pair of legs 6120 from a port tunneler in accordance with some embodiments. During a tunneling implant procedure, the port 6100 and the pair of legs 6120 are contained within an adapter 7210 in a distal end of the port tunneler. As such, the adapter 7210 restrains the pair of legs 6120 from deployment until the port 6100 exits the adapter 7210 of the port tunneler at the implantation site (e.g., port pocket) for the port 6100. Upon releasing the port 6100 from the adapter 7210 of the port tunneler with the release mechanism, the first pair of legs 6120 is configured to assume a deployed state.

Referring now to FIGS. 8A-8C, schematics are provided illustrating views of a streamlined port 8100 including a pair of wings 8120 in accordance with some embodiments. As shown, the port 8100 includes a septum 8110 opposite the pair of wings 8120. The pair of wings 8120 includes a first wing 8120*a* and a second wing 8120*b* providing a winged bullet-type shape to the port 8100. A catheter 8130 connected to the port 8100 with a catheter lock 8132 is also shown in FIGS. 8B and 8C. The port 8100 is configured for at least a tunneling implant procedure and an explant procedure with standard surgical clamps or pliers; that is, the 8100 need not the port retrievers provided herein for explant.

The septum 8110 of the streamlined port 8100 is opposite the pair of wings 8120; however, the septum 8110 can be uniquely placed in a distal end of the port 8100 as exemplified by the port 1100 of FIGS. 9A and 9B. Again, such a unique placement of a septum in a distal end of a streamlined port is an outgrowth of the port needing only a single incision for introducing, tunneling, and placing the port at an implantation site. However, because the port 8100 has a more pronounced or sharper distal end than some of the other streamlined ports provided herein, such a modification to the distal end of the port 8100 results in a less pronounced bullet-type shape of the port 8100.

The pair of wings 8120 of the streamlined port 8100 is another example of a stabilizing element of the streamlined ports provided herein, the pair of wings 8120 configured to stabilize the port 8100 from rolling about a central axis of the port 8100 in vivo, thereby maintaining needle access to the septum 8110. Due to the already small profile of the port 8100, as well as the ability of the pair of wings 8120 to stabilize the port 8100 in vivo, the port 8100 need not include collapsed and expanded states. That being said, each wing of the pair of wings 8120 can be, in some embodiments, disposed on a spring element in a wing cavity in the body of the port 8100. Like the pair of legs 6120 of the streamlined port 6100, immediately upon release of the streamlined port 8100 from an adapter of a port tunneler, each wing springs out of its cavity transitioning the port 8100 from a collapsed state to an expanded state. This is useful for expanding the footprint of the port 8100, if desired.

Referring now to FIGS. 9A, 9B, and 10, schematics are provided illustrating views of a streamlined port 9100 including an inflatable section 9120 as a stabilization element and a port tunneler 10200 for the port 9100 in accordance with some embodiments.

As shown in FIG. 10, the port tunneling system 10000 including the streamlined port 9100 and the port tunneler 10200 is configured with an inflation mechanism distributed between the port 9100 and the port tunneler 10200. The inflation mechanism allows the port 9100 to assume an initially small profile for subcutaneously tunneling the port 9100 on the port tunneler 10200 from an incision site to an implantation site. The inflation mechanism further allows the port 9100 to assume a subsequently large profile for fixing the port 9100 at the implantation site and maintaining needle access to the septum of the port 9100.

Regarding the port tunneler 10200 of FIG. 10, the port tunneler 10200 includes an inflation lumen 10222 disposed in an inflation tube, a first fitting or hub 10224 at a proximal end of the inflation tube, and a second fitting at a distal end of the inflation tube, each of which is considered part of the inflation mechanism. The inflation tube or the inflation lumen 10224 thereof is configured to fluidly connect to both a source of one or more fluids (e.g., a syringe including the one or more fluids) and the inflatable section of the streamlined port 9100 for inflating the inflatable section with the one or more fluids. The first fitting or hub 10224 at the proximal end of the inflation tube can be configured as a female Luer-tapered fitting to accept a corresponding male Luer-tapered fitting of a syringe 1001 for delivering the one or more fluids to the inflation lumen 10222. Such Luer-tapered fittings can be slipping- or locking-type Luer-tapered fittings. The second fitting at the distal end of the inflation tube can be configured as a male or female fitting in any of a number of ways to connect the inflation tube or the inflation lumen 10222 thereof to the inflatable section of the port 9100 by way of an opening in the port 9100, which opening includes a fitting corresponding to the second fitting of the inflation tube.

Regarding the port 9100 of FIGS. 9A and 9B, the port 9100 includes a septum 9110 and the inflatable section 9120. A catheter 9130 connected to the port 9100 with a catheter lock 9132 is also shown in FIGS. 9A and 9B. The septum 9110 of the streamlined port 9100 can be uniquely placed in a distal end of the port 9100 as shown in FIGS. 9A and 9B. Such a unique placement of the septum 9110 in the distal end of the port 9100 is an outgrowth of the port 9100 needing only a single incision for introducing, tunneling, and placing the port 9100 at an implantation site. Eliminating the second incision commonly used to place a port at an implantation site reduces trauma, risk of infection, and scarring at the site of the would-be second incision, thereby freeing the area for injections through the uniquely placed septum 9110 in the distal end of the port 9100. That being said, the port 9100 can alternatively include the septum 9110 in a position opposite the inflatable section 9120 of the port 9100.

The inflation mechanism distributed between the streamlined port 9100 and the port tunneler 10200 allows the port 9100 to assume the initially small profile for subcutaneously tunneling the port 9100 on the port tunneler 10200 from an incision site to an implantation site and a subsequently large profile for fixing the port 9100 at the implantation site and maintaining needle access to the septum 9110. The inflatable section 9120 of the streamlined port 9100 is another example of a stabilizing element of the streamlined ports provided herein, the inflatable section 9120 configured to stabilize the port 9100 from rolling about a central axis of the port 9100 in vivo, thereby maintaining needle access to the septum 9110.

The inflation mechanism distributed between the streamlined port 9100 and the port tunneler 10200 allows the port 9100 to assume the initially small profile for subcutaneously tunneling the port 9100 on the port tunneler 10200 from an incision site to an implantation site. The inflatable section 9120 of the port 9100, which is included as part of the inflation mechanism of the port tunneling system 10000, makes the small profile of the port 9100 possible with an uninflated state of the inflatable section 9120. That is, the inflatable section 9120 includes an uninflated state imparting or otherwise contributing to a sufficiently small profile of the port 9100 for subcutaneously tunneling the port 9100 from an incision site to an implantation site for the port 9100.

The inflation mechanism distributed between the streamlined port 9100 and the port tunneler 10200 further allows the port 9100 to assume the subsequently large profile for fixing the port 9100 at the implantation site and maintaining needle access to the septum 9110. The inflatable section 9120 of the port 9100 makes the large profile of the port 9100 possible with an inflated state of the inflatable section 9120. That is, the inflatable section 9120 further includes an inflated state configured to stabilize the port 9100 from rolling about a central axis of the port 9100 in vivo, thereby maintaining needle access to the septum 9110. In the inflated state of the inflatable section 9120, the inflatable section 9120 imparts a triangular prismatic-type shape to at least a portion of the port 9100. For example, a medial portion of the port 9100 can resemble a triangular prism when the inflatable section 9120 is in the inflated state. A transverse cross section of such a triangular prism is a triangle.

The inflatable section 9120 of the port 9100 can be configured to inflate with one or more fluids. The one or more fluids can be delivered to the inflatable section 9120 by a syringe (e.g., the syringe S of FIG. 10) by way of the inflation lumen 10222 of the port tunneler 10200, the one or more fluids selected from neat fluids and mixtures including solutions. The neat fluids can include gases such as nitrogen or argon; liquids such as water; or a combination thereof. The mixtures can include gases such as air; liquids such as mineral oil, saline, or one or more solutions of polymer(s) or polymer precursor(s); or a combination thereof.

Regarding the one or more solutions of polymer(s) or polymer precursor(s), the inflatable section 9120 can be configured to inflate by introducing a solution to the inflatable section 9120 by syringe, the solution including at least one polymer precursor (e.g., polymer precursor A) that forms a polymer with at least one other polymer precursor (e.g., polymer precursor B) after polymerization and cross linking within the inflatable section 9120. The at least one other polymer precursor (e.g., polymer precursor B) can be disposed in the inflatable section 9120 at the time of manufacturing or introduced to the inflatable section 9120 either before or after the solution including the at least one polymer precursor (e.g., polymer precursor A). Inflation of the inflatable section 9120 can include a combination of introducing one or more of the solutions of polymer precursor(s) to the inflatable section 9120 for a first expansion of the inflatable section 9120 and, subsequently, allowing the at least one polymer precursor (e.g., polymer precursor A) and the at least one other polymer precursor (e.g., polymer precursor B) to polymerize and cross link in a second expansion of the inflatable section 9120. That being said, the first and second expansions of the inflatable section 9120 can occur simultaneously, and the first and second expansions of the inflatable section 9120 can be coextensive. Inflation of the inflatable section 9120 can further include application of a low-grade, biocompatible amount of heat for the polymerization, the cross linking, or both the polymerization and cross linking. Cross linking hardens the polymer in the inflatable section 9120.

The inflatable section 9120 of the port 9100 can be configured to inflate with one or more polymers, optionally in combination with one or more of the foregoing fluids. The one or more polymers can be one or more swellable polymers disposed in the inflatable section 9120 at the time of manufacturing. The inflatable section 9120 can be configured to inflate by a combination of introducing one or more of the foregoing fluids (e.g., water, saline, etc.) to the inflatable section 9120 for a first expansion of the inflatable section 9120 and, subsequently, allowing the one or more swellable polymers to swell in the presence of the one or more fluids in a second expansion of the inflatable section 9120. That being said, swelling kinetics of the one or more swellable polymers can be such that the first and second expansions of the inflatable section 9120 occur simultaneously. In addition, the first and second expansions of the inflatable section 9120 can be coextensive.

The streamlined port 9100 can include a one-way valve configured to close off an opening to the inflation section 9120 of the port 9100 upon releasing the port 9100 from the port tunneler 10200. The one-way valve can include a diaphragm or ball configured to rest against an inside of the opening to the inflation section 9120. Pressure of an incoming inflation fluid or a male fitting at the distal end of the inflation tube of the port tunneler 10200 can hold open the one-way valve by displacing the diaphragm or ball. Once the pressure of the incoming inflation fluid or the male fitting is removed, internal pressure in the inflation section 9120 of the port 9100 presses the diaphragm or ball against the opening to the inflation section 9120 keeping the one-way valve closed. Alternatively, the one-way valve can be a flutter valve that closes off the opening to the inflation section 9120 of the port 9100 upon releasing the port 9100 from the port tunneler 10200.

With respect to implanting the streamlined port 9100 of FIGS. 9A and 9B, vascular access is established at a first incision location, and a catheter tip is advanced to a location such as the superior vena cava. The catheter is then trimmed and attached to the port 9100. The port 9100 is then placed on the port tunneler 10200 and tunneled subcutaneously to an implant location such as the upper chest. An inflation solution is then injected into the inflation lumen of the port tunneler 10200, and the inflatable section 9120 of the port 9100 is inflated to its full dimensions. The port tunneler 10200 is then removed, thereby disconnecting the port 9100 from the inflation lumen, which closes the one-way valve of the port 9100. The access site is then closed. The port 9100 is then accessed with a needle function to verify proper function.

Referring now to FIG. 11, a schematic is provided illustrating a port tunneler 11200 including a full-sized handle 11230 in accordance with some embodiments. The handle 11230 is configured to provide an operator an adequate grip for tunneling and positioning streamlined ports. With respect to the tunneling of ports, an initial tunneling path can be started with a typical tunneler. The port tunneler 11200 can be configured with sufficient bendability to follow the initial tunneling path. Furthermore, as set forth herein, a tunneling tip of a port body can be configured as aggressive for direct tunneling on a port tunneler such as the port tunneler 11200. As shown, the port tunneler 11200 further includes a release button 11232 to release a tunneling port from the adapter 11210. The release button 11232 is configured to push a deployment rod of a release mechanism in the port tunneler 11200 to disengage the port from the adapter 11210 when the release button 11232 is pushed. The port tunneler 11200 is configured to be subsequently removed from the tunneling path without disturbing the position of a catheter already placed, for example, in the superior vena cava.

Referring now to FIG. 12, a schematic is provided illustrating a sequential dilator set 12000 for a tunneling implant procedure in accordance with some embodiments. As shown, the streamlined ports such as the tunable port 1100 can be configured for implantation by way of an introducer sheath 12030 of a sequential dilator set 12000. The sequential dilator set 12000 includes, but is not limited to, a typical tunneling tool, tunneler, initial dilator, or first dilator 12010 at, for example, ⅛" in diameter; a second dilator 12020; and a final introducer sheath 12030 of a sufficient diameter for accommodating a streamlined port with a stabilizing element. In order to establish a thin-walled support sheath for implanting a streamlined port (e.g., the streamlined port 1100), a tunneling path is started at an incision site with the initial dilator 12010, which includes a flexible length extending from its proximal end for threading the rest of the dilator set 12000 thereon. In a first stage of dilation, the second dilator 12020 is threaded over the initial dilator 12010, which is ultimately removed. Next, at a second stage of dilation, the final introducer sheath is threaded over both the second dilator 12020 and the initial dilator 12010. Subsequently, the initial dilator 12010 and the second dilator 12020 are removed leaving the introducer sheath 12030 in place. The port is implanted through the introducer sheath 12030 in a port pocket at a final implant location. The introducer sheath 12030 is subsequently withdrawn, and any stabilization elements such as a pair of collapsed legs are immediately expanded to fix the port in the port pocket at the final location. The advantage of sequential dilation with the sequential dilator set 12000 is less aggressive development of dissection along the implant path, as well as better control over the final implant location. Furthermore, only a stitch or two is necessary to close the incision site, if any stitches are needed at all.

The foregoing tunneling path started with the initial dilator 12010 can be used to place a guidewire, which can then be used to tunnel the over-the-wire streamlined port 2108 to the final implant location.

Such a sequential dilator set facilitates tunneling the ports during implantation to their final implant location regardless of the explant procedure. Furthermore, such a sequential dilator set aids jugular explant procedure by running the first and second dilators over the tunneler.

Referring now to FIGS. 13 and 14, schematics are provided illustrating a port retriever 14000 including a collet 14210 and a pulling explant procedure 13000 with the port retriever 14000 in accordance with some embodiments. As shown, the port retriever 14000 includes a full-sized handle configured to provide an operator an adequate grip for retrieving streamlined ports. In addition, the handle includes a slider 14232 configured to push a final support sheath over the collet 14210 so the collet fingers of the collet 14210 can adequately clamp the port for the pulling explant procedure. The port retriever 1400 is configured for port retrieval through the same tunneling path as the tunneling implant procedure in order to eliminate scars typically associated with port-pocket port explants.

With respect to the pulling explant procedure 13000 for a port, a dilator set such as the sequential dilator set 12000 is used to run over a catheter up to a distal end of the port near a catheter lock. With the port 5100 of FIG. 13, for example, the first dilator 12010 of the sequential dilator set 12000 is run over the catheter 5130 bottoming out on the catheter lock 5132. The second dilator 12020 is run over the first dilator 12010 also bottoming out on the catheter lock 5132. After enough dilation is established, a final support sheath (e.g., the sheath 12030 of the sequential dilator set 12000) is placed and the port retriever 14000 is advanced to the port 5100 down the support sheath to engage the port 5100. Collet fingers of the collet 14210 are configured to deflect over an angled undercut on the distal end of the port 5100. The slider 14232 is configured to push the support sheath over the collet 14210. Once engaged, the port 5100 can be retracted through the support sheath as it collapses the second pair of legs 5120 into the support sheath.

Referring now to FIGS. 15A and 15B, schematics are provided illustrating a port retriever 15000 in different usage states in accordance with some embodiments. As shown, the port retriever includes a handle 15330, a port scoop 15310, and a port hook 15312, wherein FIG. 15A shows the port retriever 15000 in a retrieving state, and FIG. 15B shows the port retriever 1500 in a withdrawing state. The retrieving state of the port retriever 1500 is configured for hooking a port such as the port 2104 of FIG. 2 with the port hook 15312 of the port retriever 15000. Once the port is hooked, the handle 15330 can be closed to form the withdrawing state of the port retriever 15000. In doing so, the port is pulled onto the port scoop 15310, thereby retracting any deployed stabilization elements such as any pairs of legs. In addition, once the handle is closed, snap tabs or detents prevent the handle from opening again, thereby preventing accidental redeployment of the port upon withdrawing the port retriever 15000. Such a port retrieval is configured to facilitate port retrieval from, for example, the upper chest in a two-step procedure of the port retriever.

Referring now to FIG. 16, a schematic is provided illustrating an installation 16300 tool in accordance with some embodiments. As shown, the installation tool 16300 includes a port spoon 16310 configured to hold at least a distal end portion of a port such as the port 3100 for connecting and locking a catheter (e.g., the catheter 3130) to a proximal end portion of the port. The installation tool 16300 is further configured to facilitate installing the port in an adapter in a distal end portion of a port tunneler.

With respect to implanting a streamlined port provided herein, a desired vessel is located and accessed with an introducer needle at an access site. The access needle is removed and replaced with a guidewire. An introducer is advanced over the guidewire. The correct guidewire position is confirmed via fluoroscopy, the depth measurement on the guidewire is noted, and the guidewire is removed. Alternatively, the foregoing can be accomplished by ECG guidance. A catheter for the port is then trimmed to a correct length taking into account a distance from the access site to, for example, the superior vena cava plus the desired distance from the access site to a desired port pocket location in, for example, the upper chest. The catheter is attached to the port, which can come pre-installed on the port tunneler. The port tunneler is then inserted at the access site and tunneled to the desired port pocket location. The introducer is then removed, and the catheter is tucked into the access site. The catheter tip is confirmed through fluoroscopy, and the port is then released from the port tunneler. The port tunneler is removed, and the port is then accessed and correct flow is verified.

Further with respect to implanting a streamlined port provided herein, the port can be implanted as follows: A streamlined port is loaded onto an adapter in a distal end portion of a port tunneler. The port is inserted into an incision at a first body location, which incision is sized to require no more than one or two sutures for closing the incision. The port is subcutaneously tunneled to an implantation site at a second body location using a tip of the port. The port is released from the adapter with a release mechanism of the port tunneler. The adapter of the port tunneler is configured to retain a stabilizing element of the port in a collapsed state. Releasing the port from the adapter allows the stabilizing element of the port to assume an expanded state for stabilizing the port and maintaining needle access to a septum of the port in vivo.

In implanting the streamlined port, a heart end of a catheter is also implanted in the superior vena cava. A port end of the catheter is connected to the port and locked on the port with a catheter lock before loading the port on the adapter of the port tunneler. Connecting and locking the port end of the catheter on the port is either prior to or subsequent to implanting the heart end of the catheter in the superior vena cava.

The streamlined port is removed from the second body location with a port retriever. The port retriever includes a hook to pull the port out of the second body location by a hole in the tip of the port. Alternatively, the port is removed from the second body location with one or more standard surgical tools.

Further with respect to implanting a streamlined port provided herein, the port can be implanted as follows: An incision is made at a first body location, which incision is sized to require no more than one or two sutures for closing the incision. A tract is established to a second body location. The tract is sequentially dilated with a sequential dilator set. Subsequent to dilation with the dilator set, the sheath is left in place for loading a streamlined port. The port is loaded into a proximal end of the sheath. The port is tunneled to an implantation site at the second body location at a distal end of the sheath. The port is released from the distal end of the sheath. The sheath is configured to retain a stabilizing element of the port in a collapsed state along a length of the sheath. Releasing the port from the sheath allows the stabilizing element of the port to assume an expanded state for stabilizing the port and maintaining needle access to a septum of the port in vivo.

In implanting the streamlined port, a heart end of a catheter is also implanted in the superior vena cava. A port end of the catheter is connected to the port and locked on the port with a catheter lock before loading the port into the sheath. Connecting and locking the port end of the catheter on the port is either prior to or subsequent to implanting the heart end of the catheter in the superior vena cava.

The streamlined port is removed from the second body location with a port retriever. The port retriever includes a hook to pull the port out of the second body location by a hole in the tip of the port. Alternatively, the port is removed from the second body location with one or more standard surgical tools. Alternatively, the port is removed from the second body location with another sheath along the tract from the first body location to the second body location.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A system, comprising:
    a) a streamlined port including:
        a septum disposed over a cavity in a body of the port configured to accept a needle therethrough; and
        a stabilizing element configured to stabilize the port in vivo and maintain needle access to the septum; and
    b) a port tunneler including:
        an adapter in a distal end portion of the port tunneler configured to securely hold the port while subcutaneously tunneling the port from an incision site to an implantation site for the port; and
        a release mechanism configured to release the port from the adapter at the implantation site.

2. The system of claim 1, wherein the stabilizing element is an inflatable section of the port, the inflatable section including:
    an uninflated state imparting a profile to the port configured for subcutaneously tunneling the port from the incision site to the implantation site for the port; and
    an inflated state configured to stabilize the port from rolling about a central axis of the port in vivo, thereby maintaining needle access to the septum.

3. The system of claim 2, wherein the inflatable section is configured to inflate with one or more fluids, one or more polymers, or a combination thereof, and the port tunneler further includes an inflation lumen fluidly connected to the inflatable section for inflating the inflatable section with the one or more fluids, the one or more polymers, or the combination thereof.

4. The system of claim 3, wherein the port further includes a one-way valve configured to close off the inflatable section upon releasing the port from the port tunneler with the release mechanism.

5. The system of claim 2, wherein the inflatable section is configured to inflate by introducing a solution including at least one polymer precursor that forms a polymer with at least one other polymer precursor after polymerization and cross linking within the inflatable section.

6. The system of claim 1, wherein the stabilizing element is at least a pair of legs configured to stabilize the port from rolling about a central axis of the port in vivo, thereby maintaining needle access to the septum.

7. The system of claim 6, wherein the at least a pair of legs is configured to assume a deployed state upon releasing the port from the port tunneler with the release mechanism, and the adapter is configured to hold a proximal end portion of the port including the at least a pair of legs in a collapsed state of the at least a pair of legs.

8. The system of claim 1, wherein the stabilizing element is a winged bullet-type shape of the port configured to stabilize the port from rolling about a central axis of the port in vivo, thereby maintaining needle access to the septum.

9. The system of claim 1, further comprising:
    c) an installation tool configured to hold at least a distal end portion of the port for connecting a catheter to a proximal end portion of the port and facilitate installing the port in the adapter in the distal end portion of the port tunneler.

* * * * *